(12) United States Patent
Sahadevan

(10) Patent No.: US 9,155,910 B1
(45) Date of Patent: Oct. 13, 2015

(54) DEVICE AND METHODS FOR ADAPTIVE RESISTANCE INHIBITING INVERSE COMPTON SCATTERING MICROBEAM AND NANOBEAM RADIOSURGERY

(71) Applicant: Velayudhan Sahadevan, Beckley, WV (US)

(72) Inventor: Velayudhan Sahadevan, Beckley, WV (US)

(*) Notice: Subject to any disclaimer, the term of this patent is extended or adjusted under 35 U.S.C. 154(b) by 155 days.

(21) Appl. No.: 13/743,297

(22) Filed: Jan. 16, 2013

(51) Int. Cl.
| | | |
|---|---|---|
| *A61N 5/10* | (2006.01) | |
| *H05H 7/06* | (2006.01) | |
| *H01S 4/00* | (2006.01) | |
| *H05G 2/00* | (2006.01) | |
| *H01S 3/09* | (2006.01) | |

(52) U.S. Cl.
CPC ............... *A61N 5/1077* (2013.01); *H01S 3/09* (2013.01); *H01S 4/00* (2013.01); *H05G 2/00* (2013.01); *H05H 7/06* (2013.01)

(58) Field of Classification Search
CPC .............. H05G 2/00; H01S 3/09; H05H 7/06
USPC .......................................................... 378/119
See application file for complete search history.

(56) References Cited

U.S. PATENT DOCUMENTS

| | | | | |
|---|---|---|---|---|
| 4,827,491 | A * | 5/1989 | Barish .............................. | 378/65 |
| 5,247,562 | A * | 9/1993 | Steinbach ..................... | 378/119 |
| 5,339,347 | A * | 8/1994 | Slatkin et al. .................. | 378/65 |
| 6,332,017 | B1 * | 12/2001 | Carroll et al. ................. | 378/119 |
| 6,459,766 | B1 * | 10/2002 | Srinivasan-Rao ............. | 378/119 |
| 6,687,333 | B2 * | 2/2004 | Carroll et al. ................. | 378/119 |
| 6,867,419 | B2 * | 3/2005 | Tajima ........................ | 250/423 P |
| 6,906,338 | B2 * | 6/2005 | Tajima ........................ | 250/505.1 |
| 6,906,358 | B2 * | 6/2005 | Grein et al. .................... | 257/184 |
| 7,027,553 | B2 * | 4/2006 | Dunham et al. ................. | 378/5 |
| 7,030,398 | B2 * | 4/2006 | Tajima ........................ | 250/505.1 |
| 7,268,358 | B2 | 9/2007 | Ma | |
| 7,310,408 | B2 * | 12/2007 | Filkins et al. ................. | 378/119 |
| 7,317,192 | B2 | 1/2008 | Ma | |
| 7,317,292 | B2 * | 1/2008 | Iura et al. ....................... | 318/434 |
| 7,391,850 | B2 * | 6/2008 | Kaertner et al. ............. | 378/118 |
| 7,564,241 | B2 * | 7/2009 | Barty et al. ................... | 324/304 |
| 7,755,068 | B2 * | 7/2010 | Ma et al. ..................... | 250/492.3 |

(Continued)

OTHER PUBLICATIONS

Kuwahar, Y et al, Enhancement of autophagy is a potentiaCell Death and Disease (2011) 2, e177; doi:10.1038/cddis.2011.56; published online Jun. 30, 2011, Abstract. lines 3-5.

(Continued)

*Primary Examiner* — Charlie Y Peng

(57) ABSTRACT

This invention relates to adaptive resistance inhibiting 100 to 1,000 Gy, single fraction radiosurgery with inverse Compton scattering gamma ray microbeam and nanobeam. The distance from two adjacent microbeams or the nanobeam generate peak and valley dose. Proliferation of normal tissue's clonogenic cells from low or no dose valley region to peak dose regions makes the normal tissue tolerance to to 100 to 1,000 Gy. The collilinear electron beam and gamma ray microbeam and nanobeam are generated in microfocus carbon tubes in a tissue equivalent primary collimator. Electron beam is absorbed by the tissue equivalent primary collimator. Focusing anode and magnets and multiwalled carbon nanotubes channels the microbeam and nanobeam as focused beams. Methods of spread out or spot scanned or raster scanned collilinear gamma ray microbeam and nanobeam radiosurgery are implemented. Adaptive resistance to cancer treatment is inhibited by inactivation of cancer cell's repair capabilities.

11 Claims, 11 Drawing Sheets

(56) References Cited

U.S. PATENT DOCUMENTS

| | | | |
|---|---|---|---|
| 7,902,530 B1 * | 3/2011 | Sahadevan | 250/494.1 |
| 8,139,714 B1 | 3/2012 | Sahadevan | |
| 8,173,983 B1 * | 5/2012 | Sahadevan | 250/494.1 |
| 2010/0072405 A1 * | 3/2010 | Yu et al. | 250/493.1 |
| 2013/0168566 A1 * | 7/2013 | Blackburn et al. | 250/390.11 |

OTHER PUBLICATIONS

Ming Fan et al, Nuclear Factor-KB and Manganese Superoxide Dismutase Mediate Adaptive Radioresistance inCancer Res 2007; 67: (7). Apr. 1, 2007, 3220-3228, Abstract lines 5-20.

Kuwahar,Y et al, Enhancement of autophagy is a potential Cell Death and Disease (2011) 2, e177; doi:10.1038/cddis.2011.56; published online Jun. 30, 2011, Abstract. lines 3-5.

NF-kB Mediated HER2 Overexpression in Radiation-Adaptive Resistance,Radiat Res. Jan. 2009; 171(1): 9-21, Abstract lines 7-8 and p. 7, paragraph 3.

Minsky, B. et al.,Cancer of the Stomach, p. 826, in Text book of Radiation Oncology; Leibel & Phillips ed. 2nd Edition, 2004, Saunders, Philadelphia.

Harless, W.,Cancer treatments transform residual cancer cell phenotype, Harless W.Cancer Cell International 2011, 11:1, p. 2, paragraph 3-4, lines 1-20.

Savona, M. et al, Getting to the stem of chronic myeloid leukemia,Nature Reviews Cancer 8, 341-350 (May 2008), Abstract, lines 3-6.

Xu Qing-Yong et al, Identification of differential gene expression profiles of radioresistant lung cancerChin Med J 2008;121(18):1830-1837, Abstract, paragraph 3, lines 1-7.

Lammering, G. et al, EGFRvIII—mediated radioresistance through a strong cytoprotective response,Oncogenic (2003) 22, 5545-5553, Abstract, col. 1, lines 1-18.

Mukherjee, B., EGFRvIII and DNA Double-Strand Break Repair: A Molecular Mechanism for Radioresistance in Glioblastoma, Cancer Res 2009; 69: (10). May 15, 2009, p. 4252-4259.

Hui- Fang Li, Radiation-induced Akt activation modulates radioresistance in human glioblastoma cells,Radiation Oncology 2009, 4:43, p. 1 Abstract-conclusion, lines 1-4.

Thariat, J et. al,lntegrating Radiotherapy with EGFR antagonists and of Int J Radiat Oncol Biol Phys. Nov. 15, 2007; 69(4): 974-984, p. 3, EGFR in Radiotherapy, lines 1-9.

Yu, D et al, Redundancy of Radioresistant Signaling Patthe J of Biological Chemistry, vol. 278, No. 9, Issue of Feb. 28, pp. 6702-6709, 2003, p. 6702, Abstract, lines 1-27.

Yu, D., et al. nsulin-like Growth Factor-I Receptor Overexpression Mediates Cellular Radioresist Cancer Research, 56, 3079-3083 Aug. I, 1997J, p. 3079, Abstract, lines 1-21.

Knowlden, J. M. et al, erbB3 recruitment of insulin receptor substrate-1 impacts on insulin-like growth factor receptor sig Breast Cancer Research 2011, 13:R93, p. 2, lines 1-6.

Sachdev, D., et al., The IGF system and breast canceEndocrine-Related Cancer (2001) 8 197-209, p. 201, col. 1, lines 1-7, p. 202, IGf System and ERs, lines 1-2 and 16-19.

Garofalo C et al, Efficacy of and resistance to anti-IGF-1 R therapies in Ewing's sarcoma is dependent onOncogene 30, 2730-2740 (Jun. 16, 2011), Abstract, col. 1, lines 17-46.

Nguyen G.H et al, Cancer Stem Cell Radioresistance and Enrichment: Where Frontline Radiation Therapy May Fail in Lung aCancers 2011, 3, 1232-1252, p. 8, paragraph 5, line 1.

Nguyyen, G.H et al, Cancer Stem Cell Radioresistance and Enrichment: Where Frontline Radiation Therapy May Fail in LCancers 2011, 3, 1232-1252, p. 7, paragraph 1, lines 1-3.

Rich, J.N, Cancer Stem Cells in Radiation Resistance, Cancer Res 2007; 67:8980-8984. Published online Oct. 1, 2007, p. 8981, col. 2, paragraph 1, lines 1-2.

Gibson, D.J. et al,Design and operation of a tunable MeV-level Compton-scattering-based Accelerators 13, 070703 (2010), p. 070703-11, parag. 2, IV Conclusion, lines 1-11.

Serduc, R. I. et al, High-Precision Radiosurgical Dose Delivery by Interlaced Microbea, PLoS One, vol. 5 | Issue 2, e9028, p. 7, col. 2, paragraph 3, lines 4-18 and p. 9.

Serduc, R. I. et al, High-Precision Radiosurgical Dose Delivery by Interlaced Microbeam Arrays of High-Flux Low----, PLoS One, vol. 5| Issue 2, e9028, p. 10, Fig. 7B.

Serduc, R. I. et al, High-Precision Radiosurgical Dose Delivery by Interlaced Microbeam Arrays of High-Flux, PLoS One, vol. 5| Issue 2, e9028, p. 2, col. 1, lines 4-8.

Serduc, R. I. et al, High-Precision Radiosurgical Dose Delivery by Interlaced Microbeam Arrays of PLoS One, vol. 5 | Issue 2, e9028,p. 11, col. 2, paragraph 2, lines 1.

Laissue, J.A. et.al, Microbeam radiation therapy (MRT): Milestones—ClinicalProspects, New: Synchrotron light and Microbeam RadiationTherapy, p. 1, paragraph 3, line 7-8.

Miura, M et al, Radiosurgical palliation of aggressive murine SCCVII squamous cell carcinThe British journal of Radiology, 79 (2006), 71-75, p. 71, abstract, line 1-9.

Sawant S G et al, Adaptive Response and the Bystander Effect Induced by Radiation in C3H 10T½Cells in Culture, Radiat. Res. 156, 177-180 (2001), abstract lines 7-8.

Yi Qyi et al., Microarray analysis of DNA damage repair geneBMC Cancer 2010, 10:71, Abstract, conclusion, line 1-4.

U.S. Appl. No. 13/658,843, Sahadevan, V.

U.S. Appl. No. 13/658,843, filed Oct. 24, 2012, Sahadevan, V.

Rich, J.N, Cancer Stem Cells in Radiation Resistance, Cancer Res 2007; 67:8980-8984. Published online Oct. 1, 2007, p. 8981, paragraph 1, col. 1, lines 3-16.

Rich, J.N, Cancer Stem Cells in Radiation Resistance, Cancer Res 2007; 67:8980-8984. Published online Oct. 1, 2007, p. 8981, col. 1, and paragraph 2, lines 9-13.

Rich, J.N, Cancer Stem Cells in Radiation Resistance, Cancer Res 2007; 67:8980-8984. Published online Oct. 1, 2007, p. 8981, col. 1, and paragraph 3, lines 1-11.

Fuks. Z et. al., Engaging the vascular component of the tumor response,Cancer Cell. Aug. 2005; 8(2):89-9, Abstract, lines 3-6.

Yeom, C.J. et al, Strategies to Assess Hypoxic/HIF-1-Active Cancer Cells for the Development of Innovative RadiatCancers 2011, 3, 3610-3631, p. 3614, paragraph 5, lines 2-6.

Yeom, C.J. et al, Strategies to Assess Hypoxic/HIF-1-Active Cancer Cells for the Development of Innovative RadiatCancers 2011, 3, 3610-3631, p. 3616, lines 7-10.

Glazer, P. M. et al, Radiation Resistance in Cancer Therapy: Meeting Summary Radiation Research 176, e0016-e0021 (2011), p. e0016, col. 1, line 6 and col. 2, lines 1-6.

Fowler, J., Development of radiobiology for oncology—a personal View, Phys. Med. Biol. 51 (2006) R263-R286.

* cited by examiner

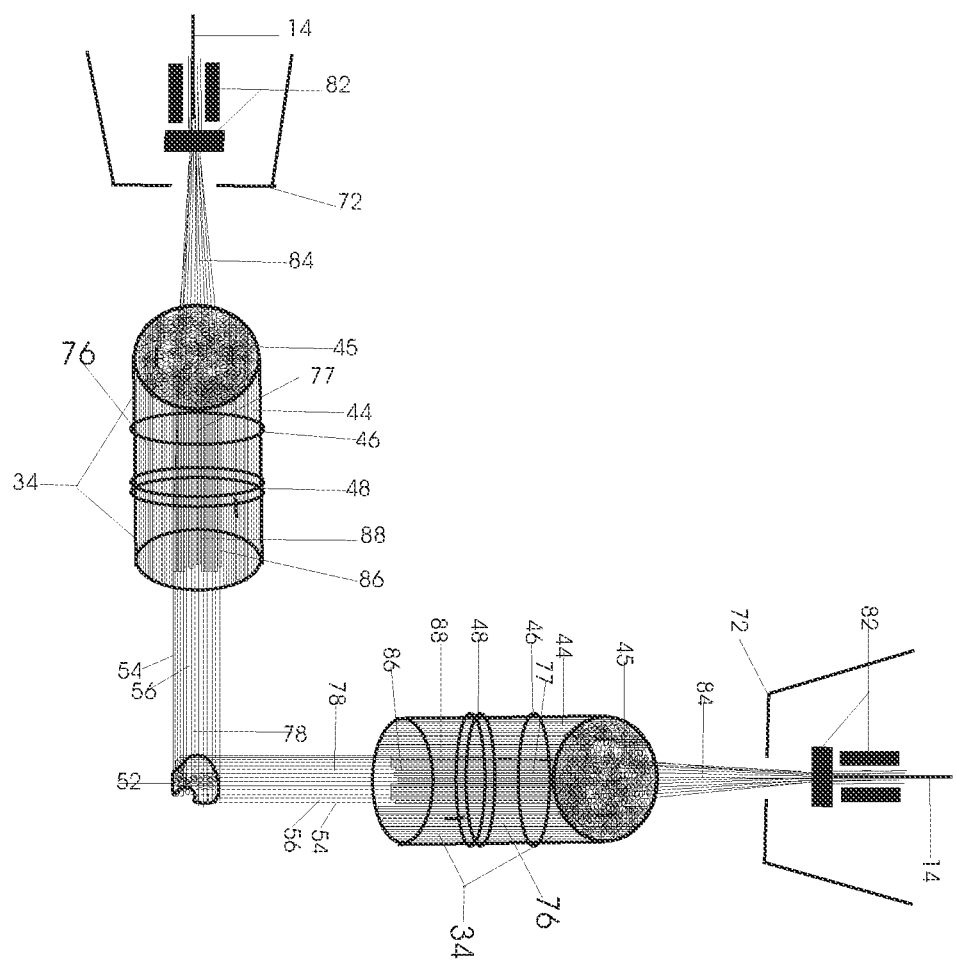

though monochromatic X-rays generated by inverse Compton Scattering could match the synchrotron generated X-rays and serve as source of micro beam and nano beam radiosurgery, no such treatment plan with inverse Compton Scattering X-rays is proposed. Likewise the proton or carbon ion based microbeam and nanobeam radiosurgery was disclosed by this applicant in (12).

DEVICE AND METHODS FOR ADAPTIVE RESISTANCE INHIBITING INVERSE COMPTON SCATTERING MICROBEAM AND NANOBEAM RADIOSURGERY

1. BACKGROUND OF THE INVENTION

In the recent past, less expensive, compact monochromatic high brilliance x-ray and gamma rays production sources were described, for biomedical use by Carroll et al (1), for phase contest imaging Kaertner et al (2) and for nuclear resonance imaging B arty et al (3). In such high brilliance X-ray source generation, high energy electron is made to interact with laser photon beam. Such high brilliance X-ray generation by inverse Compton scattering interaction of laser and electron beam has several advantages over synchrotron generated microbeam radiation therapy. Barty et al (3) describes this inverse Compton scattering X-ray as gamma rays. Like B arty et al (3), in this invention, the inverse Compton scattering radiation is referred to as Compton scattering gamma rays. Two hundred to five hundred Gy and higher dose radiation therapy with Synchrotron generated microbeam is curative even for most radiation resistant animal tumors like the glioblastoma multiforme (4). The very low energy synchrotron generated X-rays is not suitable for the treatment of deep seated human tumors. In U.S. Pat. No. 8,173,983, this applicant has described apparatus and methods for high dose and dose rate curative "All Fields Simultaneous Radiation Therapy" with monochromatic X-rays generated by inverse Compton scattering (5). In U.S. Pat. No. 8,173,983, the spent electron beam of the inverse Compton scattering is also reused to generate photon beam or electron beam for "All Fields Simultaneous Radiation Therapy" (5). However, like in present conventional radiation therapy, it uses fractionated broad beam radiation that cause normal tissue toxicity and hence the need for fractionated radiation and its limit for tolerable total dose. Inverse Compton scattering radiation renders variable energy, tunable monochromatic X-rays. In a series of US patents, Toshiki Tajima from Lawrence Livermore National Laboratory has outlined the future path for innovative radiation therapy with laser driven ion accelerators (6, 7, 8). The ion beam minimizes radiation toxicity to the skin and the normal tissue below it while it deposits energy at the spread-out Bragg Peak of the ion beam where the tumor is located. However, these innovative ion beam radiation therapy systems also use fractionated, spread-out Bragg Peak's broad beam radiation that cause still significant normal tissue toxicity and hence the need for fractionated radiation and its limit for tolerable total dose. Likewise a series of US patents by Chang Ming Ma et al from Fox Chase Cancer Center has disclosed device and methods for future radiation therapy with laser driven ion accelerators (9, 10, 11). These systems also use the methods of fractionated, spread-out Bragg Peak's broad beam for radiation that cause still significant normal tissue toxicity and hence the need for fractionated radiation and its limit for tolerable total dose. Hence, they are not suitable for single fraction 100 to 1,000 Gy and higher radiosurgery. On the contrary, in U.S. patent application Ser. No. 13/658,843, "Device and Methods for Adaptive Resistance Inhibiting Proton and Carbon Ion Microbeam and Nanobeam Radiosurgery", this applicant has disclosed the systems and methods for least toxic, single fraction, super high dose curative ion microbeam and nanobeam radiosurgery (12). Because of the only micrometers and nano meters wide segments of peak radiation with microbeam and nanobeam, the peak segment of the radiated tissue and no radiation to tissue segments in between two microbeam or nanobeam, that is the valley region, the unirradiated stem cells from the valley region readily migrates and repopulate the peak region radiated by the peak dose of the microbeam or nanobeam. It spares the normal tissue from radiation toxicity. With microbeam or nanobeams from different angels interlace at the isocentric tumor, there are no peak and valley dose region at the isocentric tumor. Hence there is no sparing of the tumor tissue from the very high dose radiation.

2. PRESENT RADIATION THERAPY'S LOW DOSE AND DOSE RATE ASSOCIATED RADIORESISTANCE

In the present practice of daily fractionated radiation therapy, the radiation is administered as 1.8 to 2 Gy at dose rate of 5 or 10 cGy (0.05 to 0.1 Gy) in about 10 to 15 min. The prolonged treatment time is due to this dose of radiation is usually administered through multiple fields, 6 or eight fields. To treat each field, the patient setup needs to be checked and the accelerator needs to be rotated to bring both the patient and the tumor in alignment with the accelerator's beam's eye view. Hence the daily treatment dose of say 1.8 Gy is further subfractionated as 6 to 8 fractions, namely to 30 or 25 cGy (0.3 to 0.25 Gy) per treatment field. If the dose rate of the accelerator were 300 cGy (3 Gy)/min and if the tumor is located at about 10 cm depth from the skin and the percent isodose were 70 at the isocentric tumor, an entrance dose of 43 cGy (0.43 Gy) is administered to each of the 6 fields of a six field setup in 8.6 seconds. Likewise, if the dose rate of the accelerator were 600 cGy (6 Gy)/min and if the tumor is located at about 10 cm depth from the skin and the percent isodose were 70 at the isocentric tumor, an entrance dose of 43 cGy (0.43 Gy) is administered to each of the 6 fields of a six field setup in 4.3 sec. Most of the present medical accelerator's dose rate is in the range of 300 to 600 cGy. Furthermore, such treatment's daily total dose of say 1.8 Gy is given as interrupted due to patient and the accelerator setup and re-setup to treat each filed in about 10 to 15 minutes. Such interrupted very low dose at dose rate of 5 or 10 cGy (0.05 or 0.1 Gy) per sec in 4 or 8 seconds will generate very poor oxidative reaction of radiation in the tumor tissue. Hence there will be very few DNA double and single strand breaks and oxidation of the protein, the hall marks of radiation reactions in the tissue.

3. MICROBEAM RADIOSURGERY

Microbeam radiosurgery (MRS) at doses ranging from 200 to 4,000 Gy and at dose rate of 16,000 Gy per second is shown to be safe to destroy the caudate nucleus in rat without damaging the normal tissue (13). For safe administration of such high dose radiation, the microbeam width is kept at 50 μm and the center to center distances of the microbeams are kept 200 to 400 μm. Its peak dose is confined within the 50 μm width microbeam and the valley dose is confined within the 200-400 μm separation of the microbeams. When the separation is 400 μm, the valley dose drops to about 10 percent of the 100 percent peak dose (13). With interlaced multiple beams from different angles and directed towards an isocentric tumor reduces the dose to the normal tissue while the isocentric tumor is treated with the combined dose of all the interlaced beams (15, 16) but each of the interlacing beam is administered sequentially. Hence it has no added advantage of additive high dose and dose rate that was described by this inventor before (17). In several laboratory animal experiments, the microbeam radiation therapy has shown its efficacy to treat most radioresistant tumors like the glioblastoma multiforme, transplanted subcutaneous murine mammary carcinoma (18) and aggressive murine SCCVII squamous cell carcinoma (19).

4. 100 TO 1,000 GY, SINGLE FRACTION MICROBEAM AND NANOBEAM RADIOSURGERY WITH MONOCHROMATIC GAMMA RAY GENERATED BY INVERSE COMPTON SCATTERING

This invention however pertains to super high dose, 100 to 1,000 Gy, single fraction—gamma ray microbeam and nanobeam radiosurgery. It is similar to 100-1,000 Gy single fraction ion microbeam and nanobeam radiosurgery but with the exception of using X-rays and gamma rays generated by inverse Compton scattering of laser and electron beams. Synchrotron generated X-ray microbeams are successfully used for curative treatment of even incurable experimental rodent glioblastoma without much normal tissue toxicity (4). However, because of its low energy, it is not suitable for clinical microbeam radiation therapy. Gamma rays generated by the inverse Compton scattering interaction of laser with high energy electron beam can have energies in the range of 1-2 MeV (20). The 1.17 and 1.33 MeV $^{60}$Co gamma rays (average energy 1.25 MeV) were the mostly available beams for clinical radiation therapy. However, the $^{60}$Co gamma rays with average energy 1.25 MeV has the clinical disadvantage of relatively higher subcutaneous dose and hence toxicity to skin and its fibrosis. It also has lesser depth dose as compared to present mostly used higher MV beams for radiation therapy. Such clinical disadvantages of 1 to 2 MeV gamma ray is eliminated in this invention by implementing the methods of microbeam and nanobeam radiation therapy in which the peak and valley dose principles associated normal tissue regeneration minimizes and or eliminates the normal tissue toxicity. The clonogenic cell migration from the unirradiated valley regions to heavily radiated peak region protects the normal tissue. The pencil microbeam and nanobeam has deeper penetration in tissue than its equivalent energy broad beam. Hence, the 1 to 2 MeV gamma ray microbeam or nanobeam generated by the inverse Compton interaction of laser and high energy electron beam has sufficient energy and normal tissue protection for clinical radiosurgery. Thus, like with ion microbeam and nanobeam radiosurgery, it also spares the normal tissue from radiation toxicity. Its single fraction, 100 to 1,000 Gy radiations sterilizes the tumor cells, including the radioresistant clonogenic cancer-stem cells. Because of the single fraction, 100 to 1,000 Gy radiations to a tumor within seconds, the tumor cells have no opportunities to develop adaptive resistance or to proliferate. However, while it is similar to super high dose single fraction ion microbeam and nanobeam radiosurgery, its radiobiological effectiveness is lesser than those with carbon ion microbeam and nanobeam radiation as it is disclosed in the U.S. patent application Ser. No. 13/658,843 by this inventor (12).

5. ADAPTIVE RESISTANCE TO RADIATION THERAPY AND CHEMOTHERAPY

Low dose and low dose rate daily fractionated radiation therapy induce adaptive response to radiation injury (22) Hela cells exposed to fractionated Neutron and X-Ray radiation from 2 to 10 Gy likewise acquires radioresistance (23). The adaptive response to radiation is evoked by a host of molecular events triggered by the oxidative process of ionizing radiation. Mouse skin pre-exposed to 10 cGy X-rays cause radioresistance to subsequent 200 cGy radiation. This adaptive resistance is mediated by the NF-kB family of proteins, the manganese superoxide dismutase, phosphorylated kinases, Cyclin B 1(24) and a number of other enzymes. Clinically relevant adaptive radioresistance is reported when HepG2-8960-R and HepG2-R from HepG2, cells are exposed to 200 Gy daily for 30 days (24). More frequent HER2 positive invasive recurrent breast tumors occur after radiation as compared to primary tumors (26). Peptic ulcer treated with radiation to a dose of 1500 to 2000 cGy by orthovoltage radiation is known to increase the risk of gastric cancer. When this radiation was combined with surgery, it increased 10 fold. (27). Like the adaptive response to radiation induced stress and its defensive response, wound healing process is an adaptive response by the injured tissue. After surgery, the epithelial mesenchymal transition (EMT) enable the epithelial cell to assume its phenotypic characteristics that enables it to migrate, digest and regeneration through matrix metalloproteinase and to resist apoptosis during such migration and regeneration. Wound healing is such a tissue process with acute inflammatory process, mobilization of molecular factors like TGF, PGF, HGF, PDGF IGF and tissue specific stem cell proliferation (28). Tyrosine kinase inhibitor refractory chronic myeloid leukemia stem cells progress to anaplastic progeny that is independent of myeloid stem cell (29).

6. ADAPTIVE RADIATION RESISTANCE TO FRACTIONATED RADIATION THERAPY

NF-kB activation and radio and chemoresistance are noted in breast cancer. HER2-(Human Epidermal Growth Factor Receptor-2) in breast cancer is known to cause aggressive tumor growth. HER2 expression can be induced by radiation in breast cancer cell lines with low basal level of HER2. The NF-KB is required for HER2 activation by radiation and the HER2 and the NF-KB are co-activated by radiation. NF-kB mediated HER-2 over expression is reported in adaptive radioresistance in breast cancer (26). HER2 mediated radioresistance is inhibited by siRNA (26). The fractionated ionizing radiation therapy at 4 Gy fractions to 60 Gy total dose to human small cell lung cancer lines induced 59 upregulated genes that were associated with DNA damage repair and 43 downregulated genes. The up-regulated genes were associated with DNA damage repair, extracellular matrix, cell adhesion and apoptosis and the 43 downregulated genes were associated with angiogenesis, immune response and calcium signaling pathways (30). The truncated epidermal growth factor receptor EGFRvIII and EGFR wild type (EGFRwt) are coexpressed in human carcinomas and glioblastoma when they are grown as xenografts but not when they are grown in vitro. A single 2 Gy radiation increased the Tyr phosphorylation 2.8 times in EGFRwt (wt-wild type). In EGFRvIII it was increased 4.3 fold. The pro-proliferative mitogen activated protein kinase in EGFRvIII was increased to 8.5 folds. Likewise, the antiapoptotic AKT/phosphatidylinositol-3-kinase pathways in EGFRvIII were increased to 3.2 folds (31). EGFRvIII is known to be a major factor in the radioresistance in glioblastoma multiforme brain tumors (32). Like EGFRvIII, Akt might be an important gene that induces increased radiation resistance in glioblastoma multiforme (33).

7. EGFR AS AN EXAMPLE OF ADAPTIVE RADIORESISTANCE IN CLINICAL PRACTICE

Adaptive radiation resistance is the cellular response to irradiative stress. It is expressed in the cells that survive the very first fraction of the usual total 30 to 40 fractionated radiation therapy. It's EGFR and TGF-α is upregulated. Within 5 to 10 min after the very first dose of 1 to 5 Gy radiations there is a 2-5 fold increase in tyrosine phosphorylation. It returns to base level value within 5-10 min. (34). Such phosphorylation after the very first fractionated dose of radiation is found only in EGFR expressing tumors. Thus it is an adaptive radiation resistance resulting from the first dose of a conventional fractionated radiation therapy regime. Hence it is an acquired or an activated radioresistance. Several EGFR inhibitors are used to overcome this adaptive radioresistance. They include cetuximab, TKIs, antisense nucleotides, other antibodies like hR3 and panitumumab. The radiation therapy combined with these agents increase the tumor response but they also become ineffective and overcoming the resistance to drugs like EGFR inhibitors is difficult (34). Hence, these inhibitors are effective only for a very short time and afterwards, the tumor re-grows more aggressively. Hence, they are not effective for cure or control cancer completely.

Cancer cells have a large number of alternative DNA, cytoplasmic and cellular radiation damage repair oncogenes and mutated of tumor suppression factors such as the mutated p53 and others. They enable the cancer cell to recover from the radiation and chemotherapy damage and become radioresistant. It is not feasible to treat a patient concomitantly with radiation and all the cancer cell proliferation inducing and mutated tumor suppressor genes inhibitors. It is an elusive objective to find any single cancer cell proliferation oncogenes and mutated tumor suppressor growth factors inhibiting drug that will overcome the adaptive resistance to radiation therapy and chemotherapy. On the other hand if a tumor is treated in a single session radiosurgery with high dose and dose rate as in this invention, this adaptive resistance to radiation therapy will not take place and many more cancer will be cured and controlled.

8. INSULIN-LIKE GROWTH FACTOR-I RECEPTOR AND ADAPTIVE RADIATION RESISTANCE

Following ionizing radiation, the Insulin-like growth factor-I receptor (IGF-IR) is known to confer clonogenic radioresistance (35). IGF-IR is known to confer radioresistance directly. Breast cancer specimen containing high levels of IGF-IR have higher incidence of tumor recurrence after lumpectomy and radiation therapy (36). Patients with breast cancer and having elevated levels of IGF-IR in their tumor specimens have early treatment failures. It-presents with recurrence and metastasis in less than 4 years (35, 36). Tamoxifen and other hormone resistant, estrogen receptor positive breast cancers are associated with IGF-IR and EGF, a member of erbB receptor family tyrosine kinases (37). It is another example of the adaptive resistance to cancer treatment, in this case, adaptive chemotherapy resistance. Increased IGF-IR can cause resistance to radiation therapy and chemotherapy (38). IGF-IR and estrogen receptor (ER) are coexpressed in some breast cancers. ER regulates transcription of IGF-I, IGF II, IGF-IR and IRS-I (39). The subset of Ewing's sarcoma is highly sensitive to anti-insulin-like growth factor (IGF)-1R therapies. However such treatments induces the Ewing's sarcoma cells to outsmart the IGF-IR inhibiting drugs like the tyrosine kinase inhibitors by switching from IGH-IR1 to its homodimer IGF-IR2 and continue synthesis AKT and ERK1/2, to maintain its malignant proliferation, migration and metastasis (39).

9. CANCER STEM CELL'S ADAPTIVE RADIATION RESISTANCE

Cancer stem cells are radioresistant and will survive from radiation induced stress more than the differentiated cancer cells (40). The histone H2A phosphorylation, the most readily recognizable marker for DNA double stand breaks is markedly reduced in Cancer Stem cell after radiation than in the differentiated cancer cell (41). Cancer stems cells in solid tumors are resistant to conventional cancer treatments (42), say it is radiation therapy or chemotherapy. The glioblastoma and colon carcinoma cancer cell surface marker CD $133^+$ is more enriched than in differentiated cancer cells. In glioblastoma, there is a three to four fold increase in CD $133^+$ cells immediately after radiation. This indicates that the surviving cancer cells after the radiation injury have relatively higher number of cancer stem cells (43). After radiation, the surviving CD $133^+$ cells in glioblastoma are capable of proliferation just like the non-radiated glioblastoma cells (44). It is an evidence for stem cell's capacity for repair after radiation injury. In glioblastomas, the degree of DNA damage caused by radiation in CD $133^+$ and CD $133^-$ cells are the same but the CD $133^+$ cells repairs the DNA damage more efficiently than in CD $133^-$ cells indicating its adaptive radiation resistance (45) and rapid recovery from radiation induced injuries. The cancer stem cells are programmed to withstand the stress caused by radiation. The presence of basal level of activation of DNA damage check point, rad 17, in CD $133^+$ cells also indicates its adaptive radioresistance. The accelerated repopulation of cancer cells, tumor recurrence and metastasis after radiation all are associated with cancer stem cell recovery after radiation. The present fractionated, 1.8 to 2 Gy per day, 5 treatments per week to a total dose of 70-80 gray is most likely exasperate the efforts to cure and control cancers due to cancer stem cell recovery, its effective survival, proliferation and eventual metastasis after the treatments.

10. HYPOXIA AND HYPOXIA INDUCIBLE FACTOR-1 AND VEGF AND ADAPTIVE RADIATION AND CHEMOTHERAPY RESISTANCE

During the course of the fractionated radiation therapy, the HIF-1 activation initiates multiple adaptive responses in the tumor cell and in the tumor microvasculature network. This pleotropic adaptive response includes both radiosensitizing the tumor cells and tumor radioresistance due to protection of the microvascular endothelium (46). The hypoxic tumors stimulate tumor microvascular angiogenesis to maintain its nutritional needs and oxygenation. It makes the conventional radiation therapy and chemotherapy mostly ineffective. It stimulates multiple gene expression like the lysyl oxidase, chemokine receptor CXXR4 and osteopoetin (47). Radiation activates HIF-1 and HIF-1 stimulates the vascular endothelial growth factor (VEGF) and the VEGF protects the endothelial cells from radiation (48). It leads to tumor microvascular proliferation, tumor growth and metastasis.

11. "RESISTANCE TO THERAPEUTIC DOSES OF RADIATION REMAINS A CHALLENGE" RADIATION RESISTANCE AND CANCER THERAPY, NATIONAL CANCER INSTITUTE WORKSHOP SUMMARY

The National Cancer Institute's workshop held on Sep. 1-3, 2010 on Radiation Resistance and cancer Therapy, it was concluded that "resistance to therapeutic doses of radiation remains a challenge. Key biological features such as tumor hypoxia, DNA damage response and checkpoint pathways, angiogenesis and vasculogenesis, cancer stem cells, tumor stroma, and immune response pathways all contribute to the complex dynamics governing tumor responses to radiation" (49). These complex features of biology of cancer cell and the difficulty to overcome the resistance to radiation therapy and also to chemotherapy are briefly discussed above. It is not possible to include all the complex defense mechanism that the cancer cell have to overcome the radiation induced stress, some of the other cellular defense against radiation injury that it can call for include the adaptive defense by means of poly(ADP-ribose) polymerase-1 (PARP), the adaptive defense by means of insulin-like growth factor-1-secretory clusterin, the adaptive defense by means of DNA-PK complex and DNA-PK subunit Ku, the adaptive defense by means of protein phosphatases, the adaptive defense by means of gamma secretase, the adaptive defense by means of Wee-1, the adaptive defense by means of small molecule c-Met, the adaptive defense by means of tyrosinekinases, the adaptive defense by means of RcQ helicase, the adaptive defense by means of terminal deoxynucleotidyl transferase (TdT), the adaptive defense by means of DNA-Polymerase X-Family, the adaptive defense by means of shRNA and SiRNA and so many other genomic expressions that are not mentioned here. It shows the complexity of the subject. Therefore, it is obvious that any single or a combination two, three or say 5 or even 10 anticancer drug combinations and the present methods of daily low dose, fractionated radiation to a total dose of 60 to 80 Gy in about 8 to ten weeks will not sterilize a tumor and its cancer cells, especially the few remaining, usually invisible cancer stem cell from proliferation, recurrence and eventual metastasis.

Examples of such evolving and differing genomic expression are well observed in metastatic breast cancer that contains coexisting estrogen receptor positive and negative components. Treating such a tumor with anti-estrogen will be beneficial to estrogen receptor positive component of the tumor if the tumor growth is solely dependent on estrogen. Unfortunately however, the estrogen receptor negative portion of the tumor will not benefit from the anti-estrogen treatment. Hence the treatment outcome will not be satisfactory. Such is the complexity of attempting to overcome the radioresistance with drugs that will inhibit one element of the cell's or a group of cell's stress defense against radiation while the other elements in the cancer cell or a group of cancer cells will counteract the beneficial effect of a particular radioresistance inhibiting drug. On the other hand, if the anti estrogen were combined with more innovative methods of radiation with super high dose and dose rate than the present "therapeutic doses" then the estrogen receptor positive and negative as well as the many other oncogene controlled tumors will be cured and controlled. Hence the conclusion of the most learned group of experts and scientists gathered at the National Cancer Institute a year ago that the "resistance to therapeutic doses of radiation remains a challenge" is one that we can attempt to overcome with the hope that there is light at the end of the tunnel. This invention is aimed to depart from the present "therapeutic doses of radiation", at daily 1.8 to 2 Gy per fractions and 3 to 6 Gy per min dose rate, five fractions a week, eight to ten weeks treatment to a total dose of 70-80 Gy with seconds to milliseconds duration 100 to 1,000 Gy radiosurgery with minimal or no toxicity to normal tissue.

12. DENATURATION OF ENZYMES ASSOCIATED WITH REPAIR OF RADIATION DAMAGE WITH HYPERTHERMIA AND SINGLE FRACTION 100 TO 1,000 GY RADIOSURGERY

In U.S. Pat. No. 8,139,714, "Few Seconds Beam on Time, Breathing Synchronized Image Guided All Fields Simultaneous Radiation Therapy Combined with Hyperthermia" this inventor has disclosed the advantages of single fraction hyperthermia combined with single fraction high dose radiation therapy (50). A number of enzymes are associated with repair of radiation damage. Just to name a few of the above named enzymes includes the NF-kB family of proteins, the manganese superoxide dismutase, phosphorylated kinases, Cyclin B 1, HER-2 (Human Epidermal Growth Factor Receptor-2), the truncated epidermal growth factor receptor EGFRvIII and EGFR wild type (EGFRwt), the pro-proliferative mitogen activated protein kinase, antiapoptotic AKT/phosphatidylinositol-3-kinase, EGFR, Insulin like growth factor (IGF) and Hypoxia Inducible Factor-1 and VEGF. The single fraction super high dose, 100 to 1,000 Gy radiations itself can denature these enzymes. Hyperthermia also denatures the enzymes associated with the radiation damage repair. Thus the combined hyperthermia and 100 to 1,000 Gy single fraction radiosurgery without much toxicity to normal tissue is a curative cancer treatment. The greatest heat radiosensitization is produced when the heat is delivered as close to the time of irradiation as possible, since a likely mechanism for the sensitizing effect is heat denaturation of the proteins (enzymes) associated with the repair of radiation damage.

13. NORMAL TISSUE SPARING 100 TO 1,000 GY SINGLE FRACTION RADIOSURGERY IN SECONDS AND ITS $\beta/\beta$ RATIO AND LATE NORMAL TISSUE COMPLICATIONS Preset radiobiology principles are better described on the basis linear quadratic, $\beta/\beta$ ratio based cell survival parameters that were developed since about the 1960. It was pioneered by Jack Fowler et al. He has illustrated its over half a century long journey through this concept and its evolution as a personal story in 2006 (51). Its fundamental principles based on fractionated radiation therapy and its cellular events forms the basic understandings of today's radiation therapy and its increasing role present curative and palliative cancer treatment. According to this concepts, single fraction large dose radiation cause more late normal tissue complications. Hence the daily fractionated radiation therapy with 1.8 to 2 Gy is elected. However, the rapidly developing stereotactic radiosurgery and intraoperative radiation therapy uses very large single fraction radiation, 20-30 Gy and higher without much late responding normal tissue toxicity. Its simplistic explanation is that in such precisely planned, most normal tissue sparing treatments, lesser normal tissue is included in the radiation field. Thus protecting the normal tissue from radiation toxicity allows administration of large single fraction dose even for today's broad beam radiosurgery. In present stereotactic radiosurgery and intraoperative radiosurgery, large broad beams are used for radiation. Radiosurgery with microbeam and nanobeam spares the normal tissue toxicity by its differential peak and valley radiation and regeneration of tissue in the peak dose region by migration of clonogenic cells from the low dose valley region. Hence safe 100 to 1,000 Gy single fraction radiosurgery within a few seconds is feasible. It defies the fundamental principles involved in the protracted broad beam fractionated radiation therapy and its associated linear quadratic, $\beta/\beta$ ratio concept.

14. BRIEF SUMMARY OF THE INVENTION

This invention teaches a systems and methods for adaptive resistance inhibiting monochromatic gamma ray microbeam and nanobeam radiosurgery. The monochromatic gamma ray microbeam and nanobeam are generated by the inverse Compton interaction of laser beam and high energy electron beam. Monochromatic high brilliance X-rays and gamma rays are generated by the inverse Compton interaction of laser beam with electron beam as described by this inventor in U.S. Pat. No. 8,173,983, (52). Similar inverse Compton monochromatic X-ray (gamma ray) generation is disclosed by other inventors, by Kaertner et al (2) and by Barty et al (3). They are referred here in their entirety. The inverse Compton scattering's collilinear x-ray-gamma ray and electron beams travels together (the term collilinear is used to describe the co-linear forward propagation of the electron beam and the X-ray photon beam as adherent together; Please refer to FIG. 1-9). The electron beam is separated from the x-ray-gamma ray with electron beam absorbing primary collimators and the X-ray-gamma ray is made microbeam or nanobeam within these primary and secondary collimators.

The pencil monochromatic collilinear electron beam and the X-ray-gamma ray is spread out with a passive scatterer. The electron beam is absorbed with a tissue equivalent universal collimator. The length of the tissue equivalent primary collimator is adjusted to the length of the depth of penetration of the electron beam in tissue. It thus absorbs and removes the electron beam that does not enter the carbon micro or nanotubes. It is also equipped with microfocus carbon tubes that are placed at a distance of one to four ratio of beam width and distance from each other. They generate the peak and valley dose.

The collilinear electron-X-ray-gamma beam that enters into the microfocus carbon tubes is focused with focusing anode and the focusing magnet. To remove the electron beam that enters the microfocus carbon tube, a sufficient length of the carbon tube is filled with tissue equivalent material. The X-ray-gamma ray microbeam or nanobeam separated from the electron beam travels through the rest of the hollow carbon nanotube towards a patient specific secondary collimator and towards the isocentric tumor. Patient specific collimators of varying size are placed upstream to the tissue equivalent universal collimator. The X-ray-gamma ray microbeam or nanobeam leaves the microfocus carbon tubes and travels towards the isocentric tumor. Arrays of parallel microbeam or nanobeam from different angles interlace at the isocentric tumor. They radiate the tumor at high dose and dose rate. The normal tissue is spared from the radiation toxicity by virtue of the peak and valley dose differential in normal tissue and migration and proliferation of the clonogenic cells from the valley region to the peak high dose region as in cases of wound healing.

Because of the adaptive resistance to radiation and chemotherapy, they are only partially effective to cure and control most cancers. Hence after radiation and chemotherapy, the tumors with residual radiation and chemotherapy resistant cancer stem cells with metastatic potentials will continue to proliferate. Super high dose, 100 to 1,000 Gy single fraction microbeam or nanobeam radiations eliminates even the last residual clonogenic cancer stem cells without damaging the surrounding normal tissue High dose and dose rate Compton scattered X-ray and gamma ray microbeam or nanobeam radiation as described in this invention also resolves the National Cancer Institute workshop's conclusion that "resistance to therapeutic doses of radiation remains a challenge. Key biological features such as tumor hypoxia, DNA damage response and checkpoint pathways, angiogenesis and vasculogenesis, cancer stem cells, tumor stroma, and immune response pathways all contribute to the complex dynamics governing tumor responses to radiation" (49). All these adaptive resistances to cancer treatment causing factors due to lower dose and lower dose daily fractionated radiation are eliminated by this inventions' high dose and dose rate, from 100 to 10,000 Gy and higher single fraction radiosurgery. Because of the very high dose and dose rate that could be achieved with Compton scattering monochromatic interlaced multiple simultaneous parallel X-ray-gamma ray microbeams or nanobeams beams and their additive dose and dose rate, radiosurgery without the interference of organ movement is made possible in this invention.

Hypoxia is known to be a major contributing factor in radioresistance. Hypoxia induced radioresistance is mediated by hypoxia inducible factor-1, (HIF-1) (45, 46). In radioresistant tumor cells, HIF-1 is extremely high and they have high potential for tumor angiogenesis, invasion metastasize and poor prognosis (46). N-Myc downstream regulated gene 2 (NDRG-2) is another HIF-1 target gene and it is associated with hypoxia inducible radioresistance (46). The inverse Compton scattering X-ray and gamma ray microbeam or nanobeam 100 to 1,000 Gy radiation of this invention overcomes the hypoxia inducible radioresistance mediated by HIF-1, NDRG-2 and HR.

Hyperthermia denatures the enzymes associated with the radiation damage repair. It is enhanced by single fraction 100 to 1,000 Gy radiosurgery The single fraction super high dose, 100 to 1,000 Gy radiations itself can denature the enzymes associated with repair of radiation damage. Thus the combined hyperthermia and 100 to 1,000 Gy single fraction radiosurgery without much toxicity to normal tissue is a curative cancer treatment.

Radiosurgery with microbeam and nanobeam spares the normal tissue toxicity by its differential peak and valley radiation and regeneration of tissue in the peak dose region by migration of clonogenic cells from the low dose valley region. Hence safe 100 to 1,000 Gy single fraction radiosurgery within a few seconds is feasible. It defies the fundamental principles involved in the protracted broad beam fractionated radiation therapy and its associated linear quadratic, $\beta/\beta$ ratio concept

What is claimed is:

1. Apparatus for inverse Compton scattering gamma ray microbeam and nanobeam radiosurgery comprising:
    a. isocentric microbeam and nanobeam generating electron linear accelerator and corresponding high energy laser source, wherein accelerator and laser source is configured to emit inverse Compton scattering gamma ray microbeam and nanobeam by collisional interaction of electron beam and the laser beam;
    b. an emergency beam stopper, a dose monitor, a primary beam collimator, focusing and defocusing quadrupole magnet, negatively charged electron and collilinear gamma ray, focusing and beam size controlling magnet, a stripper grid, alternating positively and negatively charged beam segments, deflection magnet with DC vertical dipole field, electron beam focusing magnet, positively charged collilinear electron and gamma ray beamlet, negatively charged collilinear electron/gamma ray beamlet, tissue equivalent primary collimator, tissue equivalent universal collimator, converging magnetic field in one plane, diverging magnetic field in another plane, collilinear electron and gamma rays beamlets, microfocus carbon tubes, focusing anode, focusing magnet, focused microbeam, patient specific collimator, focused microbeam and focused nanobeam;
    c. focusing and defocusing quadrupole magnets that generate a magnetic field for defocusing the Compton scattering gamma ray and electron beam in one plane and focusing it in another plane.

2. A method of adaptive resistance to cancer treatment inhibiting 100 to 1,000 Gy single fraction conformal radiosurgery with parallel inverse Compton scattering gamma ray microbeam and nanobeam consisting of:
   a. generating high flux-short-pulse monochromatic gamma rays for kGy single fraction radiosurgery;
   b. injecting electron beam and gamma ray into a defocusing, focusing and beam size controlling magnet that controls beam size as microbeam or nanobeam and their spacing from each other;
   c. positioning a treatment volume in a patient encompassing the isocentric tumor at the isocenter and conformal exposure of the radiosurgical field with parallel inverse Compton scattering gamma ray microbeam and nanobeam with a tissue equivalent collimator that generates microbeam and nanobeam and absorbs the collilinear electron beam;
   d. radiating a tumor with inverse Compton scattering gamma ray microbeam and nanobeam;
   e. radiating a tumor with parallel inverse Compton scattering gamma ray microbeam and nanobeam from orthogonal compact inverse Compton scattering accelerators simultaneously, where the intensity of the radiation from each accelerators is modulated;
   f. treating a tumor without developing adaptive resistance to radiation by single fraction kGy dose inverse Compton scattering parallel gamma ray microbeam and nanobeam from five accelerators simultaneously;
   g. applying adaptive resistance inhibiting kGy radiosurgery for cancer cell's DNA, cell membrane, mitochondria, nucleus and cellular proteins inactivation to inhibit tumor growth;
   h. applying combined hyperthermia and interlaced gamma ray microbeam and nanobeam single fraction kGy dose radiosurgery to cancer cells, its DNA, cell membrane, mitochondria, nucleus, insulin like growth factor, epidermal growth factor receptor, hypoxia inducible factor-1, vascular endothelial factor and enzymes for total ablation of the metabolic activities of the tumor and complete tumor ablation;
   i. applying interlaced gamma ray microbeam or nanobeam single fraction kGy radio surgery to inhibit adaptive accelerated proliferation of the tumor as when the tumor is treated by fractionated radiation therapy;
   j. applying interlaced gamma ray microbeam or nanobeam single fraction kGy radiosurgery to a tumor without normal tissue toxicity;
   k. applying parallel inverse Compton scattering gamma ray microbeam and nanobeam radiosurgery without the limitations of parallel, serial and undefined functional subunit's radiation sensitivity considerations by elimination of normal tissue toxicity;
   l. applying inverse Compton scattering gamma ray microbeam and nanobeam kGy single fraction radiosurgery within a single an inspiratory or expiratory cycle to avoid radiation to normal tissue due to organ movement during respiration;
   m. applying kGy single fraction conformal interlaced, inverse Compton scattering gamma ray microbeam and nanobeam radiosurgery with a patient specific collimator combined with a tissue specific primary collimator;
   n. applying a single dose kGy interlaced inverse Compton scattering gamma ray microbeam and nanobeam radiosurgery by spot scanning or raster scanning.

3. Apparatus as in claim 1, where inverse Compton scattering collilinear electron and gamma ray generating accelerator system consisting of a compact gantry mounted electron accelerator and laser photon generating source and equipped with beam spreading, focusing and defocusing magnets, microbeam and nanobeam generating magnets and tissue equivalent primary collimator and with a beam shaping patient specific collimator.

4. Apparatus as in claim 1, wherein inverse Compton scattering collilinear electron and gamma ray microbeam and nanobeam generated by splitting of inverse Compton scattering collilinear electron and gamma ray into smaller segmented beams and its splitting into microbeam or nanobeam in a tissue equivalent primary collimator that also absorbs the electron beam.

5. Apparatus as in claim 4, with a microbeam and nanobeam generating tissue equivalent primary collimator containing microfocus carbon tubes placed at a distance of 1:4 ratio of their width and distance that generates peak and valley doses of microbeam and nanobeam.

6. Apparatus as in claim 5, with microbeam and nanobeam generating tissue equivalent primary collimator and focusing anode and magnets to focus the inverse Compton scattering collilinear electron and gamma ray channeled through microfocus carbon tubes.

7. Apparatus as in claim 1, further consisting of a semi-patient specific carbon nanotube pre-collimator and focusing of inverse Compton scattering collilinear electron and gamma ray by carbon nanotube's magnetism.

8. Apparatus as in claim 1, further consisting of orthogonally placed inverse Compton scattering electron and gamma ray generating accelerators and their multiple simultaneous parallel gamma ray microbeam and nanobeams interlacing at an isocentric tumor in a patient.

9. A method of adaptive resistance to cancer treatment inhibiting 100 to 1,000 Gy single fraction conformal radiosurgery with parallel inverse Compton scattering gamma ray microbeam and nanobeam consisting of:
   a. compact inverse Compton scattering collilinear electron and gamma ray generating accelerator, configured to emit inverse Compton scattering parallel gamma ray microbeam or nanobeam for kGy single fraction radiosurgery;
   b. positioning a treatment volume in a patient encompassing the isocentric tumor at the isocenter and conformal exposure of the radiosurgical field with parallel inverse Compton scattering gamma ray microbeam and nanobeam with a tissue equivalent collimator that generates microbeam and nanobeam and absorbs the collilinear electron beam;
   c. radiating a tumor with inverse Compton scattering gamma ray microbeam and nanobeam;
   d. radiating a tumor with parallel inverse Compton scattering gamma ray microbeam and nanobeam from orthogonal compact inverse Compton scattering accelerators simultaneously, where the intensity of the radiation from each accelerators is modulated;
   e. treating a tumor without developing adaptive resistance to radiation by single fraction kGy dose inverse Compton scattering parallel gamma ray microbeam and nanobeam from five accelerators simultaneously;
   f. applying adaptive resistance inhibiting kGy radiosurgery for cancer cell's DNA, cell membrane, mitochondria, nucleus and cellular proteins inactivation to inhibit tumor growth;
   g. applying combined hyperthermia and interlaced gamma ray microbeam and nanobeam single fraction kGy dose radiosurgery to cancer cells, its DNA, cell membrane, mitochondria, nucleus, insulin like growth factor, epidermal growth factor receptor, hypoxia inducible factor- 1, vascular endothelial factor and enzymes for total ablation of the metabolic activities of the tumor and complete tumor ablation;

h. applying interlaced gamma ray microbeam or nanobeam single fraction kGy radiosurgery to inhibit adaptive accelerated proliferation of the tumor as when the tumor is treated by fractionated radiation therapy;

i. applying interlaced gamma ray microbeam or nanobeam single fraction kGy radiosurgery to a tumor without normal tissue toxicity;

j. applying parallel inverse Compton scattering gamma ray microbeam and nanobeam radiosurgery without the limitations of parallel, serial and undefined functional subunit's radiation sensitivity considerations by elimination of normal tissue toxicity;

k. applying inverse Compton scattering gamma ray microbeam and nanobeam kGy single fraction radiosurgery within a single an inspiratory or expiratory cycle to avoid radiation to normal tissue due to organ movement during respiration;

l. applying kGy single fraction conformal interlaced, inverse Compton scattering gamma ray microbeam and nanobeam radiosurgery with a patient specific collimator combined with a tissue specific primary collimator;

m. applying a single dose kGy interlaced inverse Compton scattering gamma ray microbeam and nanobeam radiosurgery by spot scanning or raster scanning.

10. A method as in claim 9 for adaptive resistance to cancer treatment inhibiting radiosurgery with interlaced gamma ray microbeam or nanobeam single fraction dose of 100 to 1,000 Gy without normal tissue toxicity.

11. A method as in claim 10 to inhibit adaptive proliferation of cancer cells as in response to conventional fractionated radiation therapy by single fraction kGy radiosurgery with interlaced gamma ray microbeam and nanobeam.

* * * * *

UNITED STATES PATENT AND TRADEMARK OFFICE
CERTIFICATE OF CORRECTION

PATENT NO. : 9,155,910 B1
APPLICATION NO. : 13/743297
DATED : October 13, 2015
INVENTOR(S) : Velayudhan Sahadevan It is certified that error appears in the above-identified patent and that said Letters Patent is hereby corrected as shown below:

Specification

Beginning at column 10, line 38, all descriptions on Figures and the Brief Summary of the invention are missing. Pages starting from 13 to 32 in the application is not included in the issued patent.

Missing pages in the application, starting from page 13 to 32. (attached)

Signed and Sealed this
Nineteenth Day of April, 2016

Michelle K. Lee
*Director of the United States Patent and Trademark Office*

15. Brief description of the drawings

Figure 3:
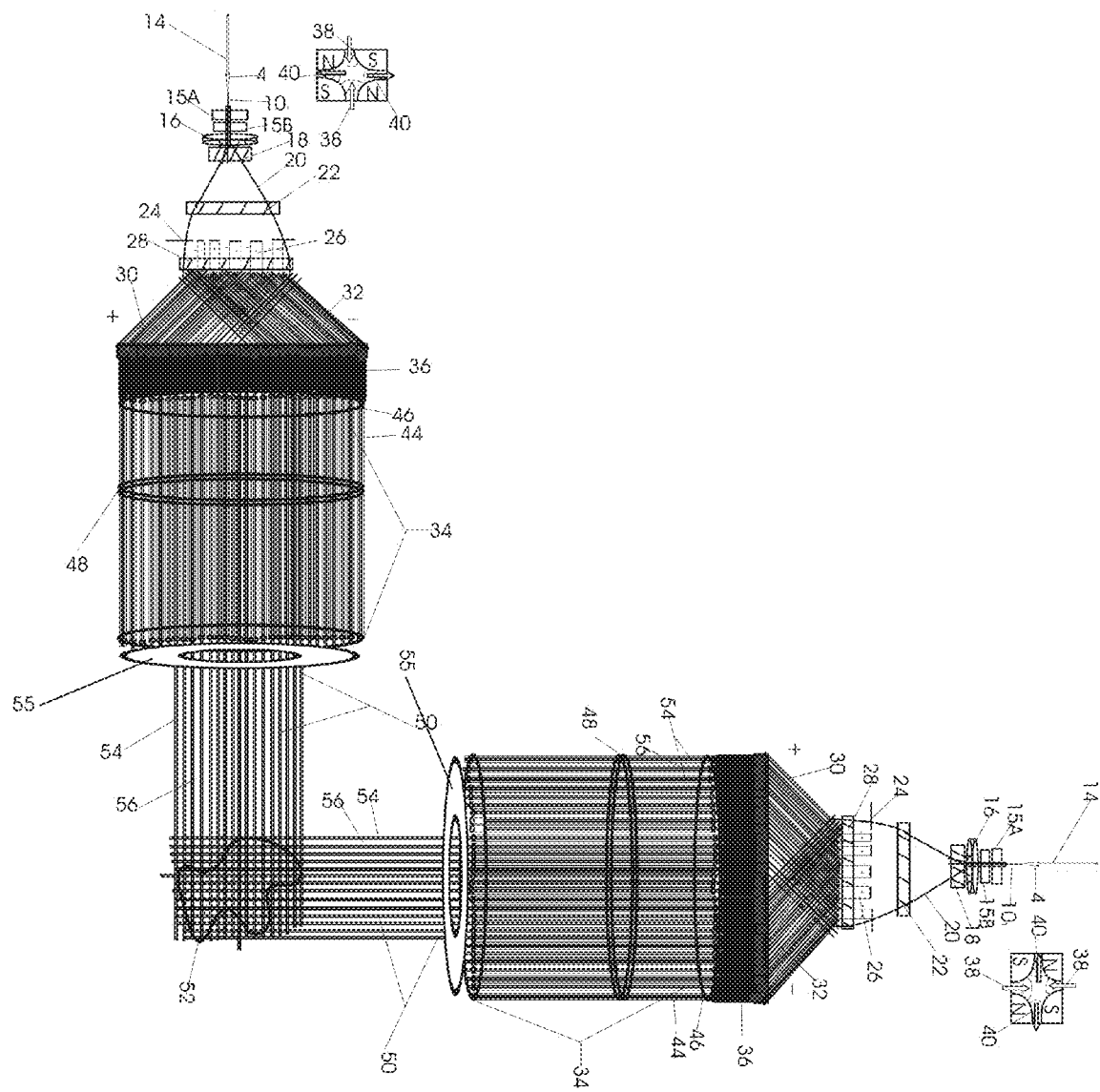

FIG. 3 illustrates two sets of interlacing parallel Collilinear electron/gamma rays beamlets 42 microbeams or nanobeams, one set from 0 degree and another set from 90 degrees and both converging at the isocentric tumor for 100 to 1,000 Gy single fraction radiosurgery with inverse Compton scattering gamma ray.

Figure 4:
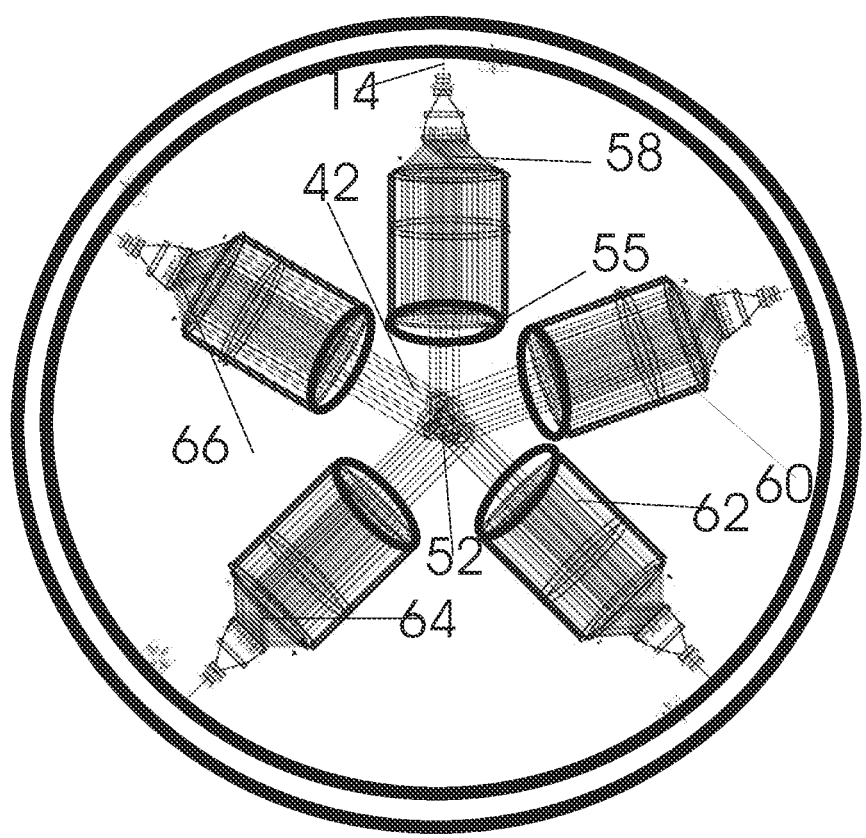

Fig. 4 shows five sets of interlacing parallel Collilinear electron/gamma rays beamlets 42 microbeams or nanobeams, all converging at the isocentric tumor for 100 to 1,000 Gy single fraction radiosurgery with inverse Compton scattering gamma ray.

Figure 5:
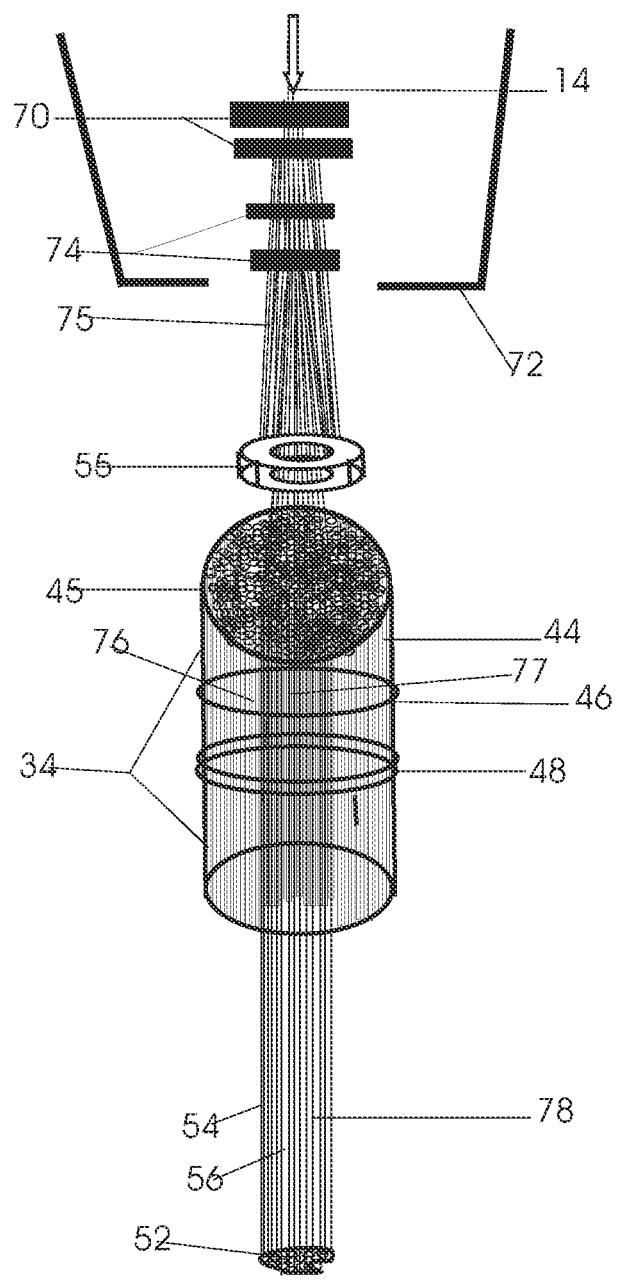

Fig. 5 illustrates the inverse Compton scattering collilinear electron beam and gamma rays microbeam and nanobeam generating cylindrical tissue equivalent primary collimator incorporated with a patient specific collimator through which the spread out inverse Compton scattering collilinear electron beam and gamma rays travels towards an isocentric tumor in a patient.

Figure 6:
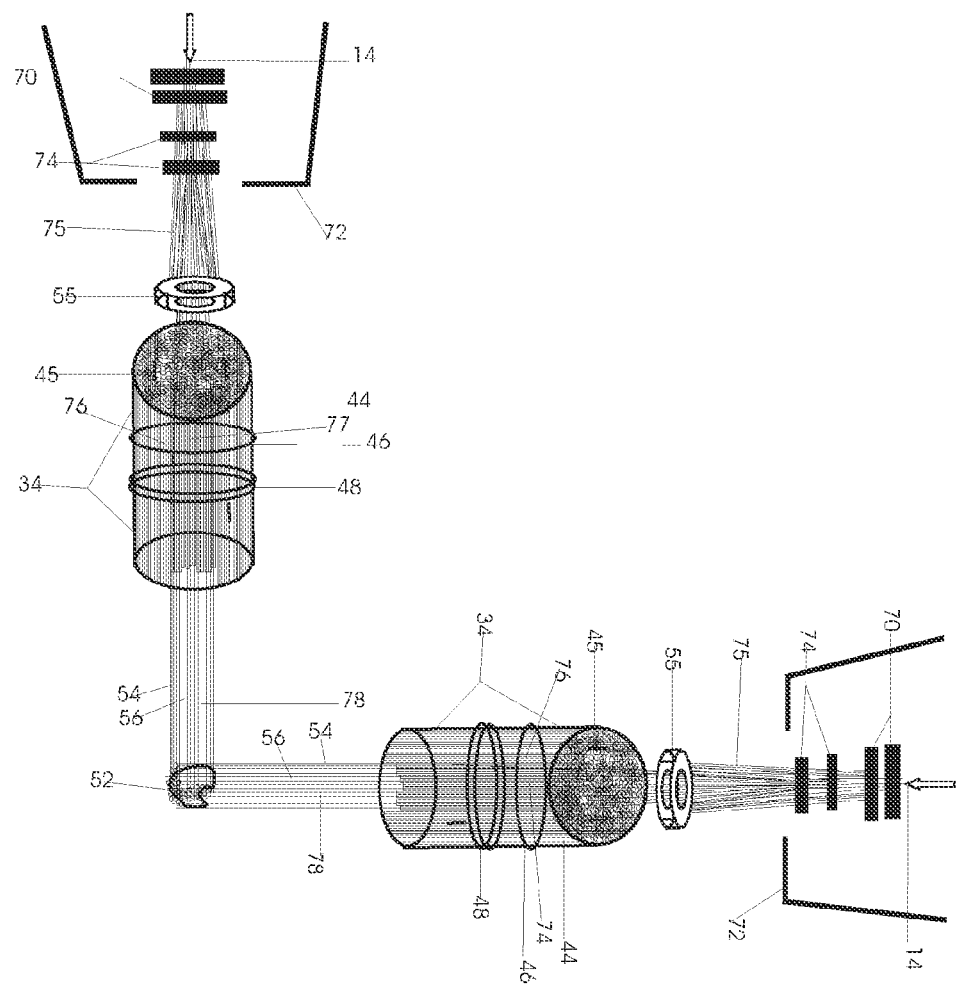

Fig. 6 shows interlacing microbeam or nanobeams from two sets of inverse Compton scattering beamlets generating systems, one at 0-degree and the other at 90-degree for simultaneously interlaced microbeam or nanobeam radiosurgery of an isocentric tumor where these beams meet and interlace with each other.

Figure 7:
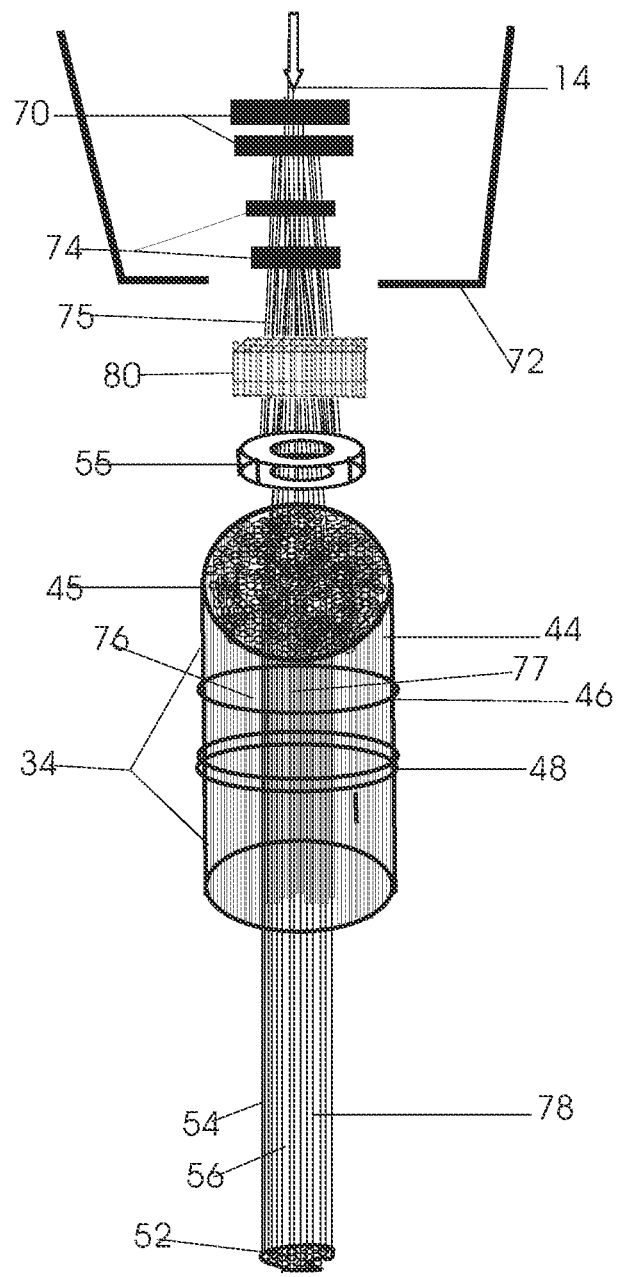

Fig. 7 is another illustration of the inverse Compton scattering collilinear electron beam and gamma rays microbeam and nanobeam generating tissue equivalent collimators incorporated with a nozzle, a semi-patient specific carbon nanotube pre-collimator and a patient specific collimator.

Figure 8:
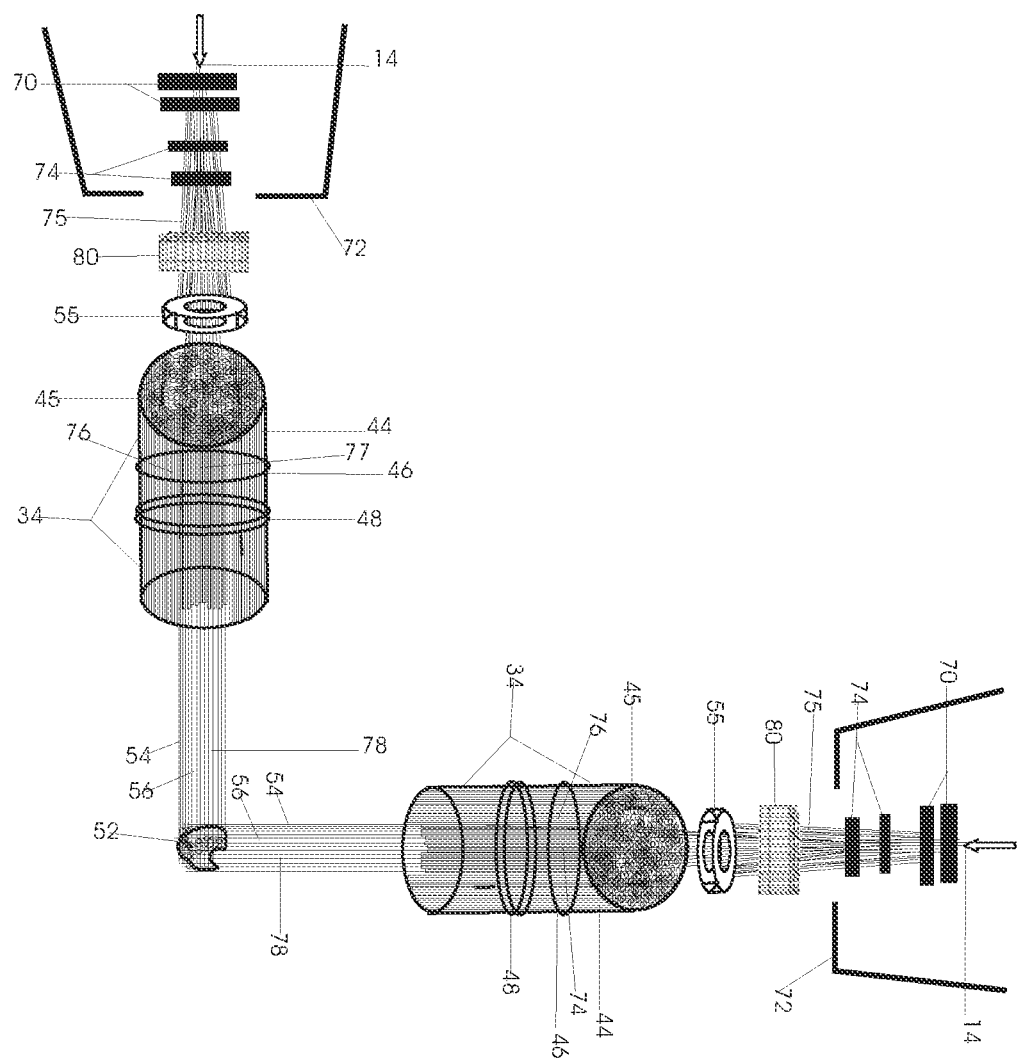

Fig. 8 shows interlacing microbeam or nanobeams from two sets of inverse Compton scattering beamlets generating systems with semi-patient specific carbon nanotube pre-collimator, one at 0-degree and the other at 90-degree for simultaneously interlaced microbeam or nanobeam radiosurgery of an isocentric tumor where these beams meet and interlace with each other.

Figure 9:
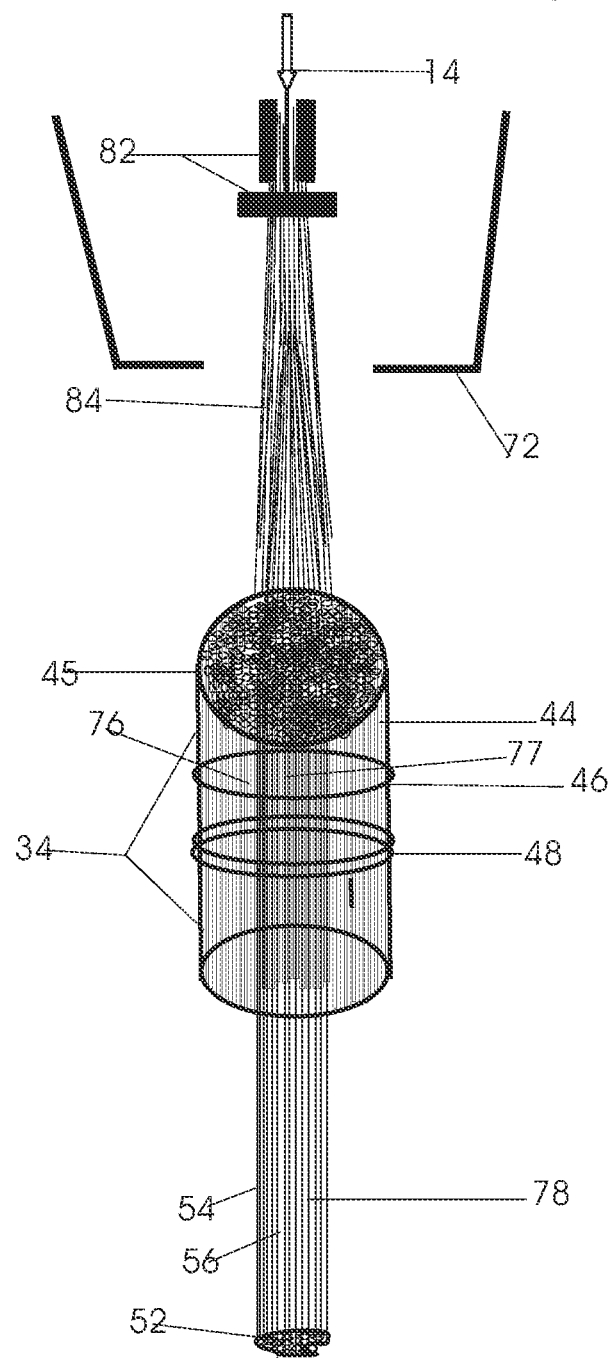

Fig. 9 illustrates active, pencil inverse Compton scattering collilinear electron beam's and gamma ray's spot scanning and generation of microbeam or nanobeam in a cylindrical tissue equivalent primary collimator for spot scanning radiosurgery with inverse Compton scattering gamma rays microbeam or nanobeam.

Figure 10:
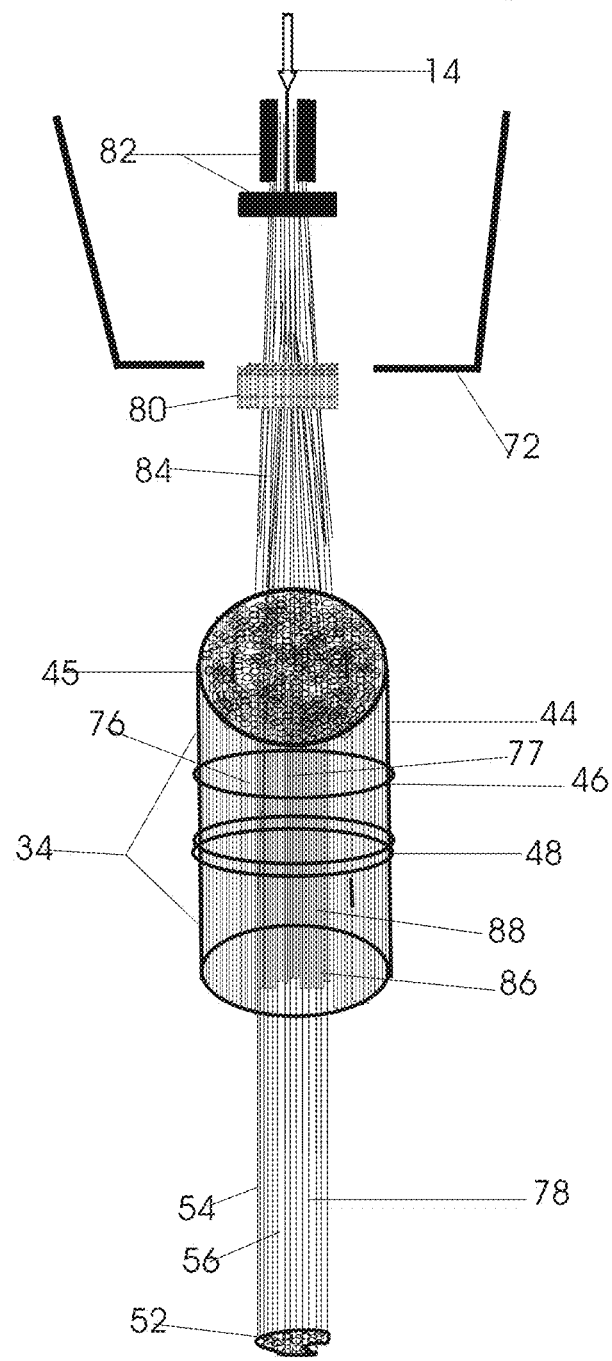

Fig. 10 shows the active, pencil inverse Compton scattering collilinear electron beam's and gamma ray's spot scanning and generation of microbeam or nanobeam in a cylindrical tissue equivalent primary collimator as in Fig. 9 but the spot scanned inverse Compton scattering collilinear electron beam and gamma rays are first treated in a semi-patient specific carbon nanotube pre-collimator as described under Fig. 7.

Fig. 11 illustrates interlacing actively spot scanned microbeam or nanobeams from two sets of inverse Compton scattering beamlets generating systems equipped with semi-patient specific carbon nanotube pre-collimator, one at 0-degree and the other at 90-degree for simultaneously interlaced microbeam or nanobeam radiosurgery of an isocentric tumor where these spot scanned beams meet and interlace with each other.

16. Reference Numerals

2. Accelerator
4. Electron beam
6. Focusing magnet
8-1. laser beam-1
8-2. laser beam-2
8-3. laser beam-3
8-4. laser beam-4
8-5. laser beam-5
8-6. laser beam-6
10. Beryllium mirror
12. Electron beam and infrared laser beam interaction

CERTIFICATE OF CORRECTION (continued)
U.S. Pat. No. 9,155,910 B1

14. Inverse Compton scattering collilinear electron beam and gamma rays

15A. Emergency beam

15B. Dose monitor

16. Collimator

18. Quadrupole magnet

20. Negatively charged electron and collilinear gamma ray

22. Focusing and beam size controlling magnet

24. Stripper grid

26. Alternating positively and negatively charged beam segments

28. Deflection magnet with DC vertical dipole field

30. Positively charged collilinear electron/gamma ray beamlet

32. Negatively charged collilinear electron/gamma ray beamlet

34. Tissue equivalent primary collimator.

36. Tissue equivalent universal collimator

38. Converging magnetic field in one plane

40. Diverging magnetic field in another plane

42. Collilinear electron/gamma rays beamlets

44. Microfocus carbon tubes

45. Microfocus carbon tube's openings

46. Focusing anode

48. Focusing magnet

50. Focused microbeam/nanobeam

52. Isocentric tumor

54. Peak dose

55. Patient specific collimator

56. Valley dose

58. Inverse Compton scattering beamlets system with tissue equivalent universal collimator-1

60. Inverse Compton scattering beamlets system with tissue equivalent universal collimator-2

62. Inverse Compton scattering beamlets system with tissue equivalent universal collimator-3

64. Inverse Compton scattering beamlets system with tissue equivalent universal collimator-4

66. Inverse Compton scattering beamlets system with tissue equivalent universal collimator-5

68. Circular non-rotating gantry

70. Passive scatterer

72. Nozzle

74. Collilinear electron beam and gamma ray microbeam or nano beam

75. Spread out inverse Compton scattering collilinear electron beam and gamma rays 76. Tissue equivalent inserts in the microfocus carbon tubes 78. Gamma ray microbeam or nanobeam 80. Semi-patient specific carbon nanotube pre-collimator 82. Scanning magnets 84. Spot scanned Compton scattering collilinear electron beam and gamma rays 86. Spot scanned and focused collilinear electron beam and gamma rays 88. Spot scanned focused collilinear electron and gamma ray microbeam/nanobeam in microfocus carbon tubes

17. Detailed Description of the Preferred Embodiments

Figure 1:
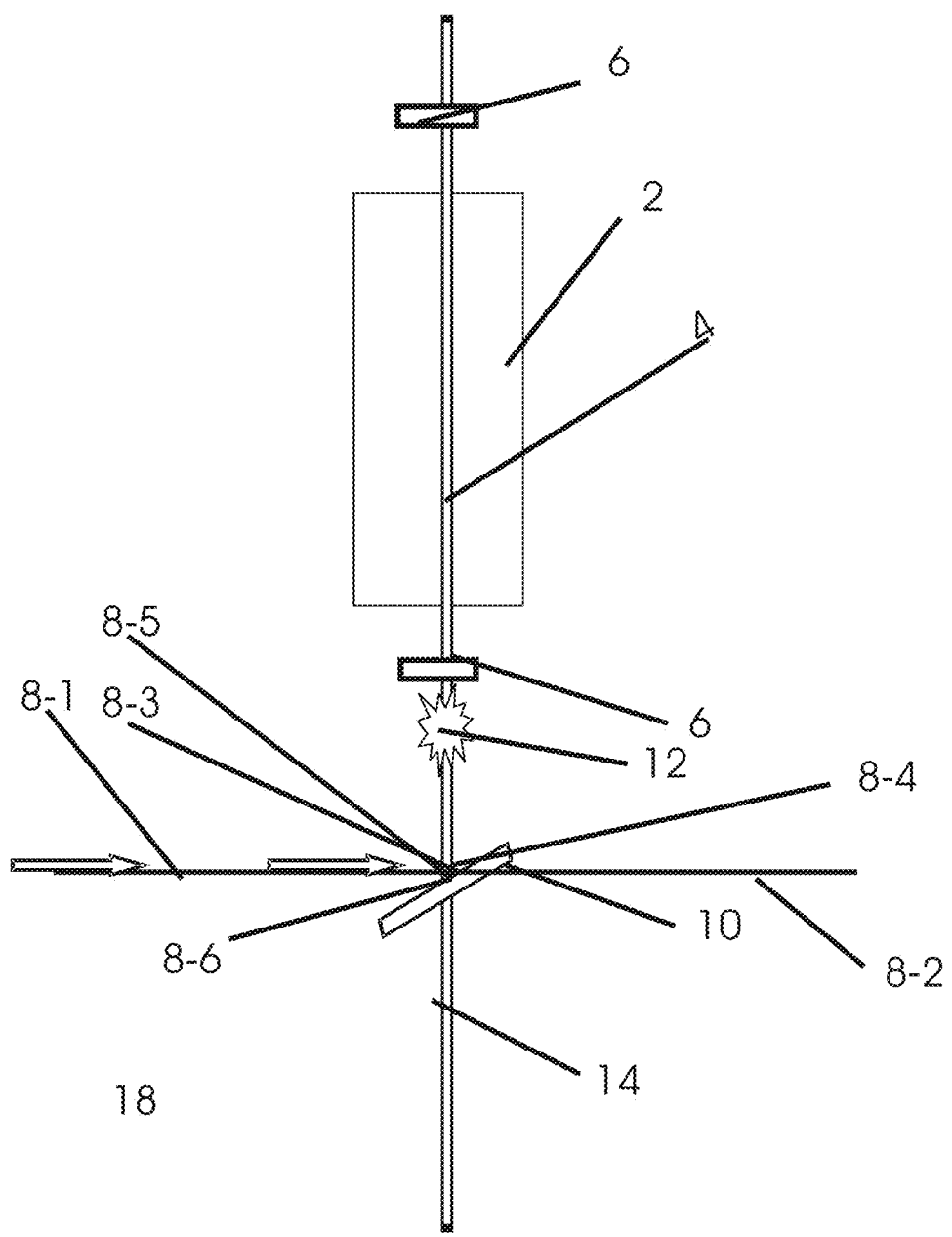
FIG. 1 illustrates an electron beam producing accelerator, electron beam interacting with laser photon beam that produce the inverse Compton scattering, monochromatic high-flux short pulse X-ray-gamma ray and its collilinear propagation with the electron beam.

FIG. 1 illustrates an electron beam producing accelerator, electron beam interacting with laser photon beam that produce the inverse Compton scattering, monochromatic high-flux short pulse X-ray-gamma ray and its collilinear propagation with the electron beam. It is disclosed in US patent 8,173,983 by this inventor. It illustrates the production of the electron beam in a photocathode. The electron beam is focused with the focusing magnet 6 and is injected into the accelerator 2. As the electron beam exits the accelerator 2, it is again focused with a second focusing magnet 6 before it interacts with an infrared laser beam 8 which is deflected with the beryllium mirror 10 towards the opposing direction of the electron beam 4. More than one laser beams, 8-1, 8-2, 8-3, 8-4, 8-5, 8-6, of varying wave lengths are used to obtain tuned, varying energy monochromatic gamma rays. Alternatively, the electron beam energy is varied to tune the monochromatic gamma-ray's energy. The electron beam 4 and the laser beam 8 collide with each other 12. This collisional interaction of electron beam and the laser beam generates the high flux-short-pulse monochromatic gamma rays. They travel almost collilinear with the electron beam's forward propagation as inverse Compton scattering collilinear electron and gamma beams 14 (arrow). They are then spread out with a passive scatterer in the process of making microbeam or nanobeam that is described in Fig. 2 below.

Figure 2:
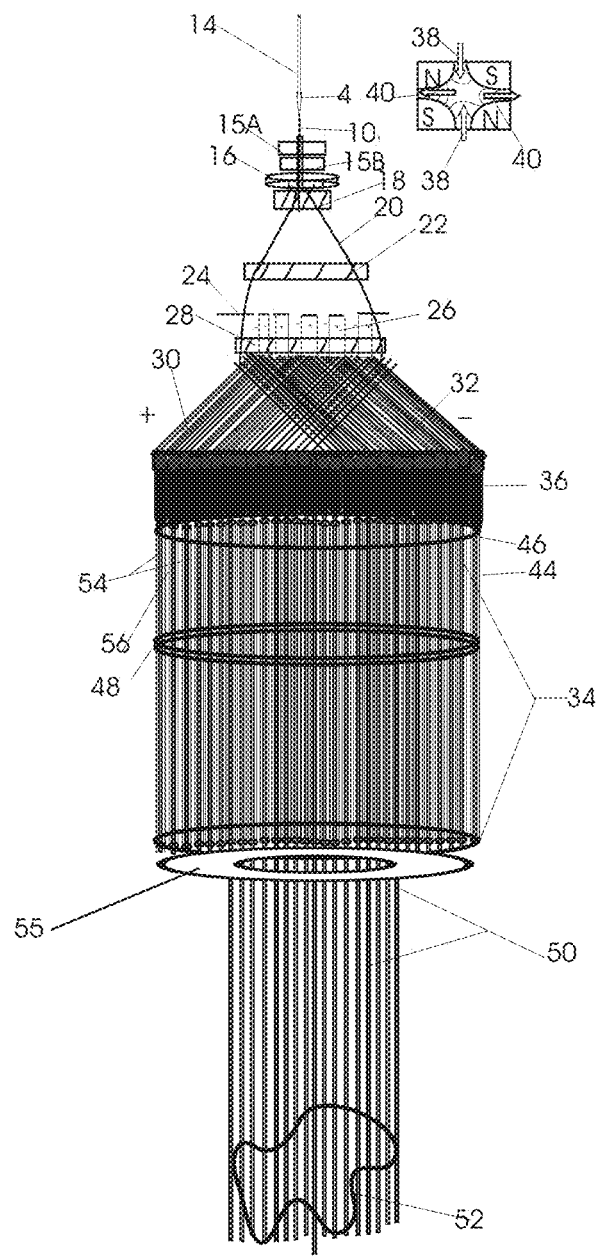
Fig. 2 shows splitting of the inverse Compton scattering gamma ray into numerous simultaneous parallel beams and generating microbeam and nanobeam with the aid of a primary collimator and microbeam and nanobeam shaping with a secondary patient specific collimator for 100 to 1,000 Gy single fraction radiosurgery with minimal or no long term radiation toxicity to normal tissue.

Fig. 2 shows splitting of the inverse Compton scattering gamma ray into numerous simultaneous parallel beams and generating microbeam and nanobeam with the aid of a primary collimator and microbeam and nanobeam shaping with a secondary patient specific collimator for 100 to 1,000 Gy single fraction radiosurgery with minimal or no long term radiation toxicity to normal tissue. The monoenergetic inverse Compton scattering gamma ray 14 is made to pass through an emergency beam stopper 15A and a dose monitor 15B and collimated by a collimator 16. This collimated beam is then defocused in one plane and focused in another plane with the quadrupole magnet 18 which spreads out the inverse Compton scattering collilinear electron and gamma rays 14 in one plane and focuses it in another plane. It is spread out in one plane and focused in another plane. The insert shows the quadrupole magnet with converging magnetic field in one plane 38 and the diverging magnetic field in another plane 40 as arranged symmetrically about the beam axis. The quadrupole magnet 18 with converging magnetic field in one plane 38 which focuses the inverse Compton scattering collilinear electron beam and gamma rays 14 and the diverging magnetic field in another plane 40 defocuses it. The one plane defocused and in another plane focused negatively charged electron and collilinear gamma ray 20 is injected into a defocusing, focusing and beam size controlling magnet 22. The split beam's size and spacing from each other is controlled with this magnet. This beam, deflected in one direction and focused in another is then passed through a stripper grid 24 that generates alternating positively and negatively charged beam segments 26. They are alternatively charged as positive and negative segments of the beam and they are passed through a deflection magnet with DC vertical dipole field 28. According to the Lawrence law of force, the positively charged collilinear electron/gamma ray beamlet 30 and the negatively charged collilinear electron/gamma ray beamlet 32 deflects to the right 32. The separating distance between each of these beamlets is dependent on the strength of dipole field. It generates numerous simultaneous parallel collilinear electron/gamma ray beamlets. These beams are subsequently processed as microbeams or nanobeams with a tissue equivalent primary collimator 34.

Down stream to the positively charged collilinear electron/gamma ray beamlet 30 and the negatively charged collilinear electron/gamma ray beamlet 32 a tissue equivalent universal collimator 36 is placed. The collilinear electron/gamma rays beamlets 42 is incident onto the universal collimator 34 which also contains microfocus carbon tubes 44 that is partially filled with tissue equivalent material for absorption of the electron beam that separates the deeper penetrating gamma ray which exits from the microfocus carbon tubes 44 at the distal end of its opening. To maintain the peak and valley dose differential as in microbeam radiation therapy, the microfocus carbon tubes 44 are placed at a distance of one to four ratio of beam width and distance from each other in tissue equivalent universal collimator 34. If the beam width is say 75 micrometers then the distance from two adjacent microfocus carbon tubes 44 is kept as 300 micrometers.

The collilinear electron/gamma rays beamlets 42 that enters into the microfocus carbon tubes 44 are focused by the focusing anode 46 and the focusing magnet 48. Focusing of the collilinear electron/gamma rays beamlets 42 traveling through the microfocus carbon tubes 44 eliminates the disadvantages of widening of the beam when it travels through a long tissue equivalent universal collimator 34. The focused microbeam/nanobeam with hardly any penumbra leave the microfocus carbon tubes 44 as focused microbeam/nanobeam 50 and travels towards the isocentric tumor 52. A patient specific collimator 55 made of tungsten powder mixture (53), Cerrobend or even the multileaf collimator is used to shape the microbeam or the nanobeam in conformity with the shape of the tumor. Different patients have different sized tumors. To shape the microbeam or nanobeam in conformity with the tumor volume, varying shape and size patient specific collimators 55 are placed downstream to the tissue equivalent primary collimator 34. The focusing anode 46 and the focusing magnet 48 keep the collilinear electron/gamma rays beamlets 42 as focused without any significant penumbra. The portion of the tissue that is radiated by the narrow parallel collilinear electron/gamma rays beamlets 42 with peak dose 54 is the peak dose regions. The tissue that is separated between the two peak radiation regions in tissue is the low or no dose region, the valley dose 56 region in tissue.

FIG. 3 illustrates two sets of interlacing parallel Collilinear electron/gamma rays beamlets 42 microbeams or nanobeams, one set from 0 degree and another set from 90 degrees and both converging at the isocentric tumor for 100 to 1,000 Gy single fraction radiosurgery with inverse Compton scattering gamma ray. Details of the microbeam collilinear electron/gamma rays 42 or nanobeam generations are described under Fig. 2. High energy, 1-2 MeV quasimonochromatic collilinear electron/gamma rays microbeam or nanobeam 42 is generated by laser- electron Compton scattering interaction. All the elements for Compton scattering gamma rays microbeam or nanobeam generation shown in this Fig. 3 are identical to those described under Fig. 2. Microbeam or nanobeam from two such accelerators, one from 0-degree and another from 90-degree are made to interlace at the isocentric tumor 52. The principles of peak and valley dose differential associated sparing of the normal tissue from radiation damage is lost at the isocentric tumor 52 where these two beams interlace. The whole tumor is radiated with the peak dose 54. There is no valley dose where these two sources of microbeams and nanobeams interlace at the isocentric tumor 52 and hence there is no tumor tissue sparing from the radiation.

Fig. 4 shows five sets of interlacing parallel Collilinear electron/gamma rays beamlets 42 microbeams or nanobeams, all converging at the isocentric tumor for 100 to 1,000 Gy single fraction radiosurgery with inverse Compton scattering gamma ray. The inverse Compton scattering collilinear electron beam and gamma rays 14 is split into collilinear electron/gamma rays beamlets 42 with microbeam and nanobeam generating tissue equivalent primary collimator 34. The inverse Compton scattering beamlets system with tissue equivalent universal collimator-1, 58, inverse Compton scattering beamlets system with tissue equivalent universal collimator-2, 60, inverse Compton scattering beamlets system with tissue equivalent universal collimator-3, 62, inverse Compton scattering beamlets system with tissue equivalent universal collimator-3, 64, inverse Compton scattering beamlets system with tissue equivalent universal collimator-5, 66 are arranged circularly on to a circular, non-rotating gantry 68. All the elements for Compton scattering gamma rays microbeam or nanobeam generation shown in this Fig. 4 are identical to those described under Fig. 2 and Fig. 3. Microbeam or nanobeam from five such accelerators interlace at the isocentric tumor 52. As described before, the principles of peak and valley dose differential associated sparing of the normal tissue from radiation damage is lost at the isocentric tumor 52 where all these beams interlace. The whole tumor is radiated with the peak dose 54. There are no valley doses where all these five sources of microbeams and nanobeams interlace. To shape the microbeam or nanobeam in conformity with the tumor volume, varying shape and size patient specific collimators 55 are placed downstream to the tissue equivalent primary collimator 34.

Fig. 5 illustrates the inverse Compton scattering collilinear electron beam and gamma rays microbeam and nanobeam generating cylindrical tissue equivalent primary collimator incorporated with a patient specific collimator through which the spread out inverse Compton scattering collilinear electron beam and gamma rays travels towards an isocentric tumor in a patient. The pencil inverse Compton scattering collilinear electron beam and gamma rays 14 is spread out by the passive scatterer 70 in a nozzle 72. The dose is monitored by the dose monitors 74. The spread out inverse Compton scattering collilinear electron beam and gamma rays 75 is incident onto the patient specific collimator 55. The tissue equivalent primary collimator 34 is equipped with microfocus carbon tubes 44. To maintain the peak and valley dose differential as in microbeam radiation therapy, the microfocus carbon tubes 44 are placed at a distance of one to four ratio of beam width and distance from each other in tissue equivalent primary collimator 34. If the beam width is say 75 micrometers then the distance from two adjacent microfocus carbon tubes 44 is kept as 300 micrometers. If the beam width were 10 micrometers, then the distance from two adjacent microfocus carbon tubes 44 is kept as 40 micrometers apart. Similar ratio of distance from microfocus carbon tubes 44 is also kept for nanobeams. If 500 nanometer width nanobeams were used for nanobeam radiation, then the distance from two adjacent microfocus carbon tubes 44 is kept as 2,000 nanometers that is 2 micrometers apart. The inverse Compton scattering collilinear electron beam and gamma rays 14 that enters into the microfocus carbon tubes 44 through microfocus carbon tube's openings 45 are focused by the focusing anode 46 and the focusing magnet 48. Such focusing of the inverse Compton scattering collilinear electron beam and gamma rays 14 traveling through the microfocus carbon tubes 44 eliminates the disadvantages of widening of the collilinear electron beam and gamma ray microbeam or nano beam 77 when it travels through the tissue equivalent primary collimator 34. Different patients have different sized tumors. Patient specific collimators 55 of varying size are placed upstream to the tissue equivalent primary collimator 34. The electron beam of the collilinear electron and gamma ray is absorbed by the tissue equivalent inserts in the microfocus carbon tubes 76. The gamma ray 78 travels towards the isocentric tumor 52. With the tissue equivalent universal collimator 34 placed downstream to patient specific collimator 55, the collilinear electron beam and gamma ray microbeam or nano beam 77 and the final gamma ray 78 is modulated in conformity with the shape and configuration of the tumor volume that is treated. Hence the microbeam/nanobeam arriving at the isocentric tumor 52 renders conformal gamma ray microbeam or nanobeam radiation to the tumor. The portion of the tissue that is radiated by the narrow parallel collilinear electron/gamma rays beamlets 42 with peak dose 54 is the peak dose regions. The tissue that is separated between the two peak radiation regions in tissue is the low or no dose region, the valley dose 56 region in tissue. The whole tumor is radiated with the peak dose 54. There are no valley doses 56 where these gamma ray microbeams or nanobeams interlace at the isocentric tumor 52 and hence there is no tumor tissue sparing from the radiation.

Fig. 6 shows interlacing microbeam or nanobeams from two sets of inverse Compton scattering beamlets generating systems, one at 0-degree and the other at 90-degree for simultaneously interlaced microbeam or nanobeam radiosurgery of an isocentric tumor where these beams meet and interlace with each other. The method of generating inverse Compton scattering collilinear electron beam and gamma rays is shown in Fig. 5. The spread out inverse Compton scattering collilinear electron beam and gamma rays 75 is processed and separated as gamma ray microbeam and nanobeam 78. The collilinear electron beam and gamma ray microbeam or nano beam 77 and the final gamma ray 78 is modulated in conformity with the shape and configuration of the tumor volume that is treated. The gamma ray microbeam and nanobeam 78 from the accelerating system at 0-degree is shown as traveling towards the isocentric tumor 52. It is interlaced with identically processed gamma ray microbeam or nanobeam 78 arriving from another identical accelerating system at 90-degree. Sparing of the normal tissue from radiation damage is lost at the isocentric tumor 52 where all the gamma ray microbeam or nanobeam 78 from the accelerating system at 0-degree and 90-degree interlace. The whole tumor is radiated with the peak dose 54. Because of the interlacing beams from 0-degree and 90-degree, there are no valley doses 56 at the isocentric tumor 52. Hence at the isocentric tumor 52, there is no tumor tissue sparing from radiation. In contrast, since there are no interlacing beams, the normal tissue is protected from radiation by proliferation of normal clonogenic stem cells from the low or no valley dose 56 regions to the peak dose 54 regions.

Fig. 7 is another illustration of the inverse Compton scattering collilinear electron beam and gamma rays microbeam and nanobeam generating tissue equivalent collimators incorporated with a nozzle, a semi-patient specific carbon nanotube pre-collimator and a patient specific collimator. The spread out inverse Compton scattering collilinear electron beam and gamma rays 75 is shown as traveling towards an isocentric tumor in a patient as in Fig. 5 but with the inverse Compton scattering collilinear electron beam and gamma rays 14 first travels through a semi-patient specific carbon nanotube pre-collimator 80. Very high efficiency channeling of high energy particle beams with energies ranging from 3 MeV to 900 GeV through multi-wall nanotube (MWNT) is reported (53). Likewise motion of high energy, kilovolt ion beam through carbon nanotubes were studied in the past (54). A number of similar previous studies on energetic ion particles such protons and electrons channeling through hollow carbon nanotubes were also reported (55). Other rapidly developing studies on proton beam and heavy ion channeling through carbon nanotube include axial channeling of high energy protons in carbon nanotubes (56), nanotubes for particle channeling, radiation and electron sources (57) and many similar ones. Vertically aligned array of pillars of multi-walled carbon nanotubes (MWCNT) are manufactured on anodized aluminum oxide (AAO) as substrate and using chemical vapor deposition of MWCNT, thermocleaning and chemical etching to exposes the MWCNT (58). Commercially available vertically aligned MWCNT are also used to guide the inverse Compton scattering collilinear electron beam and gamma rays exiting from the nozzle 72 and traveling through the semi-patient specific carbon nanotube pre-collimator 80. As the spread out inverse Compton scattering collilinear electron beam and gamma rays 75 pass through the MWCNT in the semi-patient specific carbon nanotube pre-collimator 80, the Collilinear electron/gamma rays beamlets 42 are focused within the MWCNT by the induced magnetism of the incident electron beam like the proton beam induced magnetism (59). The spread out inverse Compton scattering collilinear electron beam and gamma rays 75 enters into the MWCNT in the semi-patient specific carbon nanotube pre-collimator 80. The collilinear electron/gamma rays beamlets 42 in MWCNT is focused as nanobeams as they exit from the semi-patient specific carbon nanotube pre-collimator 80. These beams then pass through the patient specific collimator 55 and enter into the microfocus carbon tube's openings 45 and travels through the microfocus carbon tubes 44 in the tissue equivalent primary collimator 34. The beam in the microfocus carbon tube 44 is focused by the focusing anode 46 and focusing magnet 48. The electron beam of the collilinear electron and gamma ray is absorbed by the tissue equivalent inserts in the microfocus carbon tubes 76. The gamma ray microbeam or nanobeam 78 separated from the electron beam travels towards the isocentric tumor 52. With the tissue equivalent primary collimator 34 placed downstream to patient specific collimator 55, the collilinear electron beam and gamma ray microbeam or nano beam 77 and the final gamma ray 78 is modulated in conformity with the shape and configuration of the tumor volume that is treated. Hence the microbeam/nanobeam arriving at the isocentric tumor 52 renders conformal gamma ray microbeam or nanobeam radiation to the tumor.

The portion of the tissue that is radiated by the narrow parallel collilinear electron/gamma rays beamlets 42 with peak dose 54 is the peak dose regions. The tissue that is separated between the two peak radiation regions in tissue is the low or no dose region, the valley dose 56.

Fig. 8 shows interlacing microbeam or nanobeams from two sets of inverse Compton scattering beamlets generating systems with semi-patient specific carbon nanotube pre-collimator, one at 0-degree and the other at 90-degree for simultaneously interlaced microbeam or nanobeam radiosurgery of an isocentric tumor where these beams meet and interlace with each other. The method of radiosurgery with two accelerating systems without semi-patient specific carbon nanotube pre-collimator 80 is described under Fig. 5. In Fig. 6, the spread out inverse Compton scattering collilinear electron beam and gamma rays 75 is shown as passing through the MWCNT in the semi-patient specific carbon nanotube pre-collimator 80. The Collilinear electron/gamma rays beamlets 42 are focused within the MWCNT by the induced magnetism of the incident electron beam. As described before under Fig. 5 the spread out inverse Compton scattering collilinear electron beam and gamma rays 75 is processed and separated as gamma ray microbeam and nanobeam 78. The collilinear electron beam and gamma ray microbeam or nano beam 77 and the final gamma ray 78 is modulated in conformity with the shape and configuration of the tumor volume that is treated. The gamma ray microbeam and nanobeam 78 from the accelerating system with semi-patient specific carbon nanotube pre-collimator 80 at 0-degree is shown as traveling towards the isocentric tumor 52. It is interlaced with identically processed gamma ray microbeam or nanobeam 78 arriving from another identical accelerating system at 90-degree. Sparing of the normal tissue from radiation damage is lost at the isocentric tumor 52 where all the gamma ray microbeam or nanobeam 78 from the accelerating system at 0-degree and 90-degree interlace. The whole tumor is radiated with the peak dose 54. There are no valley doses 56 where these gamma ray microbeams or nanobeams interlace at the isocentric tumor 52 and hence there is no tumor tissue sparing from the radiation. In contrast, since there are no interlacing beams, the normal tissue is protected from radiation by proliferation of normal clonogenic stem cells from the low or no valley dose 56 regions to the peak dose 54 regions.

Fig. 9 illustrates active, pencil inverse Compton scattering collilinear electron beam's and gamma ray's spot scanning and or raster scanning and generation of microbeam or nanobeam in a cylindrical tissue equivalent primary collimator for spot scanning radiosurgery with inverse Compton scattering gamma rays microbeam or nanobeam. The basic principles of proton microbeam and nanobeam generation with a tissue equivalent universal collimator 34 are described under Fig. 2. The pencil inverse Compton scattering collilinear electron beams and gamma rays 14 is scanned with the scanning magnets 82 as in ion beam spot scanning for radiation therapy. The presence of collilinear electron beam in inverse Compton scattering's gamma rays makes such spot scanning possible. The scanned Compton scattering collilinear electron beam and gamma rays 84 exits from the nozzle 72 and enters into the microfocus carbon tubes 44 though the microfocus carbon tube's openings 45. The collilinear electron/gamma rays beamlets 42 in microfocus carbon tubes 44 is focused with focusing anode 46 and focusing magnet 48. This spot scanned and focused collilinear electron beam and gamma rays 86 pass through the microfocus carbon tubes 44. The spot canned and focused collilinear electron beams and gamma ray's micro beam or nanobeam 86 in microfocus carbon tubes 44 is almost without any penumbra. The electron beam of the collilinear electron and gamma ray is absorbed by the tissue equivalent inserts in the microfocus carbon tubes 76. The gamma ray microbeam or nanobeam 78 is separated from the electron beam. It travels towards the isocentric tumor 52. With the tissue equivalent primary collimator 34 and spot scanning of the collilinear electron beam and gamma ray microbeam or nano beam 77 and the final separation of the gamma ray 78 from the electron but still the gamma ray staying as spot scanned beam makes it possible to modulate the final gamma ray microbeam or nanobeam 78 in conformity with the shape and configuration of the tumor volume that is treated. Hence the gamma ray microbeam/nanobeam 78 arriving at the isocentric tumor 52 renders conformal gamma ray microbeam or nanobeam radiation to the tumor. The peak dose 54 is the microbeam or nanobeam peak dose regions. The tissue that is separated between the two peak radiation regions in tissue is the low or no dose region, the valley dose 56. The presence of collilinear electron beam in inverse Compton scattering's gamma rays also makes the raster scanning radiation therapy that is known in the art possible.

Fig. 10 shows the active, pencil inverse Compton scattering collilinear electron beam's and gamma ray's spot scanning and generation of microbeam or nanobeam in a cylindrical tissue equivalent primary collimator as in Fig. 9 but the spot scanned inverse Compton scattering collilinear electron beam and gamma rays are first treated in a semi-patient specific carbon nanotube pre-collimator as described under Fig. 7. The spot scanned inverse Compton scattering collilinear electron beam and gamma rays 84 is shown as passing through a semi-patient specific carbon nanotube pre-collimator 80. Very high efficiency channeling of high energy particle beams with energies ranging from 3 MeV to 900 GeV through MWNT) is known (53). Likewise motion of high energy, kilovolt ion beam through carbon nanotubes were studied in the past (54). A number of similar previous studies on energetic ion particles such as protons and electrons channeling through hollow carbon nanotubes are also reported in the past (55). Other rapidly developing studies on proton beam and heavy ion channeling through carbon nanotube include axial channeling of high energy protons in carbon nanotubes (56), nanotubes for particle channeling, radiation and electron sources (57) and many similar ones. Commercially available vertically aligned MWCNT are used as the semi-patient specific carbon nanotube pre-collimator 80. The inverse Compton scattering collilinear electron beam and gamma rays exiting from the nozzle 72 pass through the semi-patient specific carbon nanotube pre-collimator 80. As the spot scanned inverse Compton scattering collilinear electron beam and gamma rays 84 pass through the MWCNT in the semi-patient specific carbon nanotube pre-collimator 80, the collilinear electron/gamma rays beamlets 42 are focused within the MWCNT by the induced magnetism of the incident electron beam like the proton beam induced magnetism (59). The collilinear electron/gamma rays beamlets 42 in MWCNT is focused as nanobeams as they exit from the semi-patient specific carbon nanotube pre-collimator 80. These spot scanned beams then enter into the microfocus carbon tube's openings 45 and travels through the microfocus carbon tubes 44 in the tissue equivalent primary collimator 34. The spot scanned beam in the microfocus carbon tube 44 is focused by the focusing anode 46 and focusing magnet 48. The spot scanned and focused collilinear electron beam and gamma rays 86 passes through the microfocus carbon tube 44. The spot scanned focused collilinear electron and gamma ray microbeam/nanobeam in microfocus carbon tubes 88 remains as focused in microfocus carbon tube 44. The electron beam of the collilinear electron and gamma ray is absorbed by the tissue equivalent inserts in the microfocus carbon tubes 76. The gamma ray microbeam or nanobeam 78 separated from the electron beam and it travels towards the isocentric tumor 52. The collilinear electron beam and gamma ray microbeam or nano beam 77 and the final gamma ray 78 are modulated in conformity with the shape and configuration of the tumor volume that is treated. Hence the spot scanned gamma ray microbeam/nanobeam arriving at the isocentric tumor 52 renders conformal gamma ray microbeam or nanobeam radiation to the tumor. The portion of the tissue that is radiated by the narrow parallel gamma rays beamlets 42 with peak dose 54 is the peak dose regions. The tissue that is separated between the two peak radiation regions in tissue is the low or no dose region, the valley dose 56. The presence of collilinear electron beam in inverse Compton scattering's gamma rays also makes the raster scanning radiation therapy that is known in the art possible.

Fig. 11 illustrates interlacing actively spot scanned microbeam or nanobeams from two sets of inverse Compton scattering beamlets generating systems equipped with semi-patient specific carbon nanotube pre-collimator, one at 0-degree and the other at 90-degree for simultaneously interlaced microbeam or nanobeam radiosurgery of an isocentric tumor where these spot scanned beams meet and interlace with each other. Similar method of radiosurgery with two accelerating systems also equipped with semi-patient specific carbon nanotube pre-collimator 80 but with spread out beams is described under Fig. 8. In this instance, the scanning magnets 82 spot scans the inverse Compton scattering collilinear electron beam and gamma rays 14. The spot scanned Compton scattering collilinear electron beam and gamma rays 84 is shown as passing through the MWCNT in the semi-patient specific carbon nanotube pre-collimator 80. The spot scanned Compton scattering collilinear electron beam and gamma rays 84 is focused within the MWCNT by the induced magnetism of the incident electron beam. The spot scanned Compton scattering collilinear electron beam and gamma rays 84 is processed and separated as gamma ray microbeam and nanobeam 78. The gamma ray microbeam and nanobeam 78 from the accelerating system with semi-patient specific carbon nanotube pre-collimator 80 at 0-degree is shown as traveling towards the isocentric tumor 52. It is interlaced with identically spot scanned gamma ray microbeam or nanobeam 78 arriving from another identical accelerating system at 90-degree. Sparing of the normal tissue from radiation damage is lost at the isocentric tumor 52 where all the gamma ray microbeam or nanobeam 78 from the accelerating system at 0-degree and 90-degree interlace. The spot scanned and focused collilinear electron beam and gamma rays 86 passes through the microfocus carbon tube 44. The spot scanned focused collilinear electron and gamma ray microbeam/nanobeam in microfocus carbon tubes 88 remains as focused in microfocus carbon tube 44. The electron beam of the collilinear electron and gamma ray is absorbed by the tissue equivalent inserts in the microfocus carbon tubes 76. The gamma ray microbeam or nanobeam 78 is separated from the electron beam. It travels towards the isocentric tumor 52. The collilinear electron beam and gamma ray microbeam or nano beam 77 and the final gamma ray 78 are modulated in conformity with the shape and configuration of the tumor volume that is treated. Hence the spot scanned gamma ray microbeam/nanobeam arriving at the isocentric tumor 52 renders conformal gamma ray microbeam or nanobeam radiation to the tumor. The portion of the tissue that is radiated by the narrow parallel gamma rays beamlets 42 with peak dose 54 is the peak dose regions. The tissue that is separated between the two peak radiation regions in tissue is the low or no dose region, the valley dose 56. The whole tumor is radiated with the peak dose 54. There are no valley doses 56 where these spot scanned gamma ray microbeams or nanobeams interlace at the isocentric tumor 52. Hence, there is no tumor tissue sparing from the radiation. In contrast, since there are no interlacing beams in normal tissue, the normal tissue is protected from radiation by proliferation of normal clonogenic stem cells from the low or no valley dose 56 regions to the peak dose 54 regions. The presence of collilinear electron beam in inverse Compton scattering's gamma rays also makes the raster scanning radiation therapy possible. It is known in the art.

18. Methods of Operation

High dose and dose rate, adaptive resistance inhibiting radiosurgery with interlaced inverse Compton scattering gamma rays parallel microbeam or nanobeam

Interlaced parallel gamma ray microbeam or nanobeam is generated by inverse Compton scattering of high energy laser beam and electron beam is described under Fig. 1 through Fig. 8. The inverse Compton scattering collilinear electron beam and gamma rays beam is split into several sub-beams and their subsequent treatment in a tissue equivalent primary collimator to generate microbeam or nanobeam is described. Treating a tumor with 1 to 2 MeV gamma ray microbeams or nanobeam generated by the inverse Compton scattering of high energy laser and electron beam and treating an isocentric tumor with interlaced gamma ray microbeam and nanobeam is described under Fig. 3, Fig. 4, Fig. 6 and in Fig. 8. Alternatively, the tumor is treated with spot scanned inverse Compton scattering gamma ray as illustrated under Fig. 9, Fig. 10 and Fig. 11. The isocentric tumor is treated with interlaced parallel microbeam or nanobeam at high dose and dose rate, 100 to 1,000 Gy and 4,000 to 10,000 Gy with least toxicity to normal tissue. The principles of peak and valley dose of microbeam or nano beam facilitates such normal tissue sparing super high dose single fraction radiosurgery. Radiosurgery at doses of 100-1,000 Gy or 4,000 to 10,000 Gy with interlaced, cross firing multiple simultaneous inverse Compton scattering gamma ray's microbeam or nanobeam is given in a few seconds, within a respiratory cycle. The normal tissue outside the tumor is spared from toxic effects of radiation by the methods of peak and valley dose microbeam or nanobeam radiation. Migration of normal clonogenic stem cells from the low or no dose valley regions to the peak radiation dose regions heals the radiation damage in the peak dose regions of the normal tissue. Because of the micrometer and nanometer wide peak dose regions and healing of the radiation damage by proliferation of normal cells from valley dose region, all the tissues with parallel, serial or undefined FSUs have the same radiation effects and tolerance to radiation.

This method of radiation inactivates a host of DNA repairing enzymes and acts as both DNA strand breaking and oxidative protein damaging radiation therapy. Conventional daily 2 Gy fractions radiotherapy do not damage much of the cellular enzymes activity. It is a superior method of enzyme inactivating cancer therapy than all of the more toxic and expensive enzyme inactivating chemotherapy.

The methods of radiosurgery are well established. Patients who are able to follow instructions of the clinical staffs are placed onto the treatment table as immobilized. Radiosurgery is done within seconds that is in less than one breathing cycle's duration. It avoids the organ movements associated uncertainties in radiation therapy deliveries.

A tissue equivalent primary collimator 34 is equipped with microfocus carbon tubes 44 that modulate the incoming collilinear electron and gamma rays into microbeam or nanobeam. The collilinear electron beam and the gamma rays 74 in the microfocus carbon tubes 44 are focused with anode 46 and focusing magnet 48. Such focused collilinear electron beam- gamma ray- microbeam/nanobeam 74 hardly has any penumbra. The width and separation of the microbeam or the nanobeam from each other is used to generate the peak dose 54 and valley dose 56 regions. Treatment field is shaped by patient specific collimator 55 or by microbeam or nanobeam spot scanning methods. Different patients have different sized tumors. Patient specific collimators 55 of varying size are placed upstream to the tissue equivalent primary collimator 34. In this instance, only those beams shaped by the patient specific collimator passes through the wider tissue equivalent primary collimator 34 placed downstream to the patient specific collimator 55. The collilinear electron beam and gamma ray microbeam or nano beam 74 leave the microfocus carbon tubes 44 as focused microbeam/nanobeam and travels towards the isocentric tumor 52. Alternatively, the tumor is treated with spot scanned microbeam or nanobeam. The presence of collilinear electron beam in inverse Compton scattering radiation from the interaction of high energy laser and electron beam allows implementing the methods of spot scanned or raster scanned gamma ray microbeam radiation therapy and radiosurgery. The interlaced microbeam/nanobeam arriving at the isocentric tumor is used for conformal gamma ray microbeam/nanobeam radiation to the tumor.

In an alternative method of generating fine focused nanobeam, the spread out or spot scanned Compton scattering collilinear electron beam and gamma ray from in a treatment heads nozzle of the accelerating system is made to travel through a semi-patient specific multi walled carbon nanotube pre-collimator 80. The fine focused nanobeam exiting from the semi-patient specific multi walled carbon nanotube pre-collimator 80 enters into the microfocus carbon tubes 44 in the tissue equivalent primary collimator 34. It is maintained as focused with the anode 46 and focusing magnet 48. Such fine focused microbeam/nanobeam travels towards the isocentric tumor 52 and radiates the tumor in its 3-D conformity.

The active, pencil proton beam spot scanning or raster scanning is used for conformal inverse Compton scattering gamma ray microbeam or nanobeam radiation therapy. The pencil collilinear electron beam and gamma ray microbeam or nanobeam is scanned into the microfocus carbon nanotube 44 with preliminary scanning magnets 82. The collilinear electron/gamma rays beamlets 42 in microfocus carbon tube 44 is focused with focusing anode 46 and focusing magnet 48. This spot scanned focused collilinear electron and gamma ray microbeam/nanobeam 88 in microfocus carbon tubes 44 exits from it almost without any penumbra. It travels toward the isocentric tumor as spot scanned beam and radiates the tumor as in active spot scanned proton beam radiation therapy known in the art. To take advantages of peak and valley dose differentials as in high dose and dose rate microbeam radiation therapy, the beam width and distance of the carbon tubes from each other is maintained at a ratio of 1:4.

Additional beam processing with a semi-patient specific carbon nanotube pre-collimator containing MWCNT pre-collimator as shown in Fig. 7, Fig. 8, Fig. 10 and in Fig. 11. They further improve the active spot scanned and raster scanned inverse Compton gamma ray radiotherapy. In this instance, the spot or raster scanning is at the carbon nanotube's opening sites, not at the tumor as in conventional active spot scanning or raster scanning methods used in proton or ion radiation therapy. The collilinear electron beam is absorbed by the tissue equivalent inserts in the microfocus carbon tubes 76. It separates the gamma ray from the collilinear electron beam. The gamma ray microbeam or nanobeam 78 exits from the microfocus carbon tubes. After exiting from the microfocus carbon tubes 44 they travel toward the isocentric tumor 52 and radiates the tumor.

The present preferred embodiments of this invention are described here; however other modifications could be made without departing from the scope of this invention. The apparatus, methods, procedures and treatments are exemplary and are not intended as limitations on the scope of the invention. Other variations will appear to those skilled in the art and are contemplated to be within the scope of the appended claims.